US012329739B2

(12) United States Patent
Jeoffreys et al.

(10) Patent No.: US 12,329,739 B2
(45) Date of Patent: *Jun. 17, 2025

(54) ISOFLAVONOID COMPOUNDS AND METHODS FOR THE TREATMENT OF CANCER

(71) Applicant: Aardvark Therapeutics, Inc., San Diego, CA (US)

(72) Inventors: George Jeoffreys, Baulkham Hills (AU); Alison Johnson, Drummoyne (AU); Andrew Heaton, Alexandria (AU); Ofir Moreno, Poway, CA (US)

(73) Assignee: Aardvark Therapeutic, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/363,328

(22) Filed: Aug. 1, 2023

(65) Prior Publication Data

US 2023/0372287 A1 Nov. 23, 2023

Related U.S. Application Data

(63) Continuation of application No. 18/154,267, filed on Jan. 13, 2023, now abandoned, which is a continuation of application No. 17/023,681, filed on Sep. 17, 2020, now Pat. No. 11,583,514, which is a continuation of application No. 16/129,589, filed on Sep. 12, 2018, now abandoned, which is a continuation of application No. 15/456,182, filed on Mar. 10, 2017, now Pat. No. 10,105,346, which is a continuation of application No. 13/881,609, filed as application No. PCT/US2011/058815 on Nov. 1, 2011, now Pat. No. 9,663,484.

(60) Provisional application No. 61/408,972, filed on Nov. 1, 2010.

(51) Int. Cl.
| | |
|---|---|
| *A61K 31/353* | (2006.01) |
| *A61K 9/00* | (2006.01) |
| *A61K 9/51* | (2006.01) |
| *A61K 31/337* | (2006.01) |
| *A61K 31/555* | (2006.01) |
| *A61K 33/243* | (2019.01) |
| *A61K 45/06* | (2006.01) |
| *A61K 47/40* | (2006.01) |
| *A61P 35/00* | (2006.01) |
| *C07D 311/58* | (2006.01) |

(52) U.S. Cl.
CPC ......... *A61K 31/353* (2013.01); *A61K 9/0019* (2013.01); *A61K 9/5161* (2013.01); *A61K 31/337* (2013.01); *A61K 31/555* (2013.01); *A61K 33/243* (2019.01); *A61K 45/06* (2013.01); *A61K 47/40* (2013.01); *C07D 311/58* (2013.01)

(58) Field of Classification Search
CPC ...... C07D 311/58; A61K 31/353; A61P 35/00
USPC ......................................... 514/456; 549/406
See application file for complete search history.

(56) References Cited

U.S. PATENT DOCUMENTS

| | | |
|---|---|---|
| 3,340,276 A | 9/1967 | Carney et al. |
| 3,471,520 A | 10/1969 | Klaus et al. |
| 3,535,344 A | 10/1970 | Klaus et al. |
| 4,157,984 A | 6/1979 | Zilliken |
| 4,218,489 A | 8/1980 | Zilliken |
| 4,232,122 A | 11/1980 | Zilliken |
| 4,234,577 A | 11/1980 | Zilliken |
| 4,366,082 A | 12/1982 | Zilliken |
| 4,366,248 A | 12/1982 | Zilliken |
| 4,368,264 A | 1/1983 | Zilliken |
| 4,390,559 A | 6/1983 | Zilliken |
| 4,447,622 A | 5/1984 | Salman et al. |
| 4,644,012 A | 2/1987 | Tsuda et al. |
| 4,814,346 A | 3/1989 | Albert et al. |
| 5,024,998 A | 6/1991 | Bodor |
| 5,059,609 A | 10/1991 | Eggler et al. |
| 5,134,127 A | 7/1992 | Stella et al. |
| 5,280,040 A | 1/1994 | Labroo et al. |
| 5,376,645 A | 12/1994 | Stella et al. |
| 5,389,646 A | 2/1995 | Labroo |
| 5,464,862 A | 11/1995 | Labroo et al. |
| 5,696,149 A | 12/1997 | Korsgaard et al. |
| 5,726,202 A | 3/1998 | Shalmi et al. |
| 5,756,539 A | 5/1998 | Skrumsager et al. |
| 5,780,503 A | 7/1998 | Biftu et al. |
| 5,849,461 A | 12/1998 | Hatakeyama et al. |
| 5,874,418 A | 2/1999 | Stella et al. |
| 5,883,118 A | 3/1999 | Shalmi et al. |
| 5,919,817 A | 7/1999 | Jacobsen et al. |
| 5,958,967 A | 9/1999 | Jacobsen et al. |
| 5,985,306 A | 11/1999 | Jacobsen et al. |
| 5,994,390 A | 11/1999 | Jacobsen et al. |

(Continued)

FOREIGN PATENT DOCUMENTS

| | | |
|---|---|---|
| CA | 2581316 A1 | 3/2006 |
| EP | 0267155 A2 | 5/1988 |

(Continued)

OTHER PUBLICATIONS

Co-pending U.S. Appl. No. 18/340,308, filed Jun. 23, 2023.*

(Continued)

*Primary Examiner* — Irina Neagu
(74) *Attorney, Agent, or Firm* — McNeill PLLC

(57) ABSTRACT

Provided herein is a pharmaceutical composition comprising at least one isoflavonoid. Also provided herein are methods of treating cancer, sensitizing cancer cells, and inducing apoptosis in cancer cells by administering such compositions.

18 Claims, No Drawings

(56) References Cited

U.S. PATENT DOCUMENTS

| | | |
|---|---|---|
| 5,998,451 A | 12/1999 | Eggler et al. |
| 6,005,003 A | 12/1999 | Nique |
| 6,043,269 A | 3/2000 | Jacobsen et al. |
| 6,316,494 B1 | 11/2001 | Jacobsen et al. |
| 6,479,467 B1 | 11/2002 | Buchanan et al. |
| 6,509,323 B1 | 1/2003 | Davis |
| 6,610,671 B2 | 8/2003 | Buchanan et al. |
| 6,610,733 B2 | 8/2003 | Park et al. |
| 6,645,951 B1 | 11/2003 | Jo et al. |
| 6,649,648 B1 | 11/2003 | Kelly et al. |
| 6,660,804 B1 | 12/2003 | Weltrowski et al. |
| 7,056,952 B1 | 6/2006 | Joannou |
| 7,202,273 B2 | 4/2007 | Kelly et al. |
| 7,601,855 B2 | 10/2009 | Heaton et al. |
| 7,906,554 B2 | 3/2011 | Kelly et al. |
| 8,080,675 B2 * | 12/2011 | Heaton ............... A61K 31/655 549/399 |
| 8,084,628 B2 * | 12/2011 | Heaton ............... A23L 2/52 549/403 |
| 8,163,795 B2 * | 4/2012 | Heaton ............... A61K 31/704 549/399 |
| 8,461,361 B2 * | 6/2013 | Heaton ............... A61K 31/704 549/399 |
| 8,697,891 B2 | 4/2014 | Heaton et al. |
| 8,957,109 B2 * | 2/2015 | Heaton ............... A61K 31/655 549/399 |
| 9,138,478 B2 | 9/2015 | Heaton et al. |
| 9,198,895 B2 * | 12/2015 | Heaton ............... A61K 31/4745 |
| 9,381,186 B2 | 7/2016 | Heaton et al. |
| 9,663,484 B2 * | 5/2017 | Jeoffreys ............... A61K 9/0019 |
| 9,708,283 B2 * | 7/2017 | Moreno ............... A61K 47/40 |
| 9,981,936 B2 * | 5/2018 | Moreno ............... A61K 31/353 |
| 10,105,346 B2 * | 10/2018 | Jeoffreys ............... A61K 9/0019 |
| 10,369,132 B2 * | 8/2019 | Moreno ............... A61K 9/5161 |
| 10,973,799 B2 * | 4/2021 | Moreno ............... A61P 43/00 |
| 11,583,514 B2 * | 2/2023 | Jeoffreys ............... A61P 35/00 |
| 11,723,893 B2 * | 8/2023 | Moreno ............... A61K 45/06 514/649 |
| 2002/0128468 A1 | 9/2002 | Buchanan et al. |
| 2004/0063663 A1 | 4/2004 | Buchanan et al. |
| 2004/0106575 A1 | 6/2004 | Zhang et al. |
| 2004/0109888 A1 | 6/2004 | Pun et al. |
| 2004/0209825 A1 | 10/2004 | Lahey et al. |
| 2006/0074126 A1 * | 4/2006 | Heaton ............... C07D 311/58 549/406 |
| 2006/0074127 A1 | 4/2006 | Heaton et al. |
| 2006/0167037 A1 | 7/2006 | Kelly et al. |
| 2006/0167083 A1 | 7/2006 | Kelly |
| 2006/0183728 A1 | 8/2006 | Kelly et al. |
| 2007/0155695 A1 | 7/2007 | Wirth et al. |
| 2008/0014249 A1 | 1/2008 | Heaton et al. |
| 2008/0069900 A1 | 3/2008 | Kelly et al. |
| 2009/0317490 A1 | 12/2009 | Heaton et al. |
| 2010/0130598 A1 | 5/2010 | Brown et al. |
| 2010/0152284 A1 | 6/2010 | Brown et al. |
| 2010/0173983 A1 | 7/2010 | Brown et al. |
| 2012/0004296 A1 | 1/2012 | Heaton et al. |
| 2012/0039917 A1 | 2/2012 | Husband et al. |
| 2012/0114766 A1 | 5/2012 | Heaton et al. |
| 2012/0172424 A1 | 7/2012 | Heaton et al. |
| 2012/0251630 A1 | 10/2012 | Alvero et al. |
| 2014/0170243 A1 | 6/2014 | Heaton et al. |
| 2015/0238458 A1 | 8/2015 | Heaton et al. |
| 2015/0352074 A1 | 12/2015 | Heaton et al. |
| 2016/0136129 A1 | 5/2016 | Heaton et al. |
| 2016/0287555 A1 | 10/2016 | Heaton et al. |
| 2017/0246142 A1 | 8/2017 | Jeoffreys et al. |
| 2017/0342044 A1 | 11/2017 | Moreno |
| 2018/0237411 A1 | 8/2018 | Moreno |
| 2019/0142790 A1 | 5/2019 | Jeoffreys et al. |
| 2023/0372287 A1 | 11/2023 | Jeoffreys et al. |

FOREIGN PATENT DOCUMENTS

| | | |
|---|---|---|
| EP | 0313295 A2 | 4/1989 |
| EP | 0470310 A1 | 2/1992 |
| EP | 0955286 A1 | 11/1999 |
| GB | 1433013 | 4/1976 |
| GB | 1433013 A | 4/1976 |
| JP | 2000502507 A | 5/2000 |
| JP | 2001502706 A | 2/2001 |
| JP | 2001502711 A | 2/2001 |
| JP | 2002529372 A | 9/2002 |
| JP | 2006096734 A | 4/2006 |
| JP | 2008513376 A | 5/2008 |
| JP | 2012144537 A | 8/2012 |
| JP | 2014237638 A | 12/2014 |
| WO | WO-8002098 A1 | 10/1980 |
| WO | WO-9408986 A1 | 4/1994 |
| WO | WO-9420099 A1 | 9/1994 |
| WO | WO-9621442 A1 | 7/1996 |
| WO | WO-9621443 A1 | 7/1996 |
| WO | WO-9621444 A1 | 7/1996 |
| WO | WO-9622091 A1 | 7/1996 |
| WO | WO-9622092 A1 | 7/1996 |
| WO | WO-9622093 A1 | 7/1996 |
| WO | WO-9725035 A1 | 7/1997 |
| WO | WO-9725036 A1 | 7/1997 |
| WO | WO-9725037 A1 | 7/1997 |
| WO | WO-9725038 A1 | 7/1997 |
| WO | WO-9802154 A1 | 1/1998 |
| WO | WO-9802156 A1 | 1/1998 |
| WO | WO-9808503 A1 | 3/1998 |
| WO | WO-9817662 A1 | 4/1998 |
| WO | WO-9818770 A1 | 5/1998 |
| WO | WO-9818771 A1 | 5/1998 |
| WO | WO-9818772 A1 | 5/1998 |
| WO | WO-9818773 A1 | 5/1998 |
| WO | WO-9818774 A1 | 5/1998 |
| WO | WO-9818775 A1 | 5/1998 |
| WO | WO-9818776 A1 | 5/1998 |
| WO | WO-9818778 A1 | 5/1998 |
| WO | WO-9818779 A1 | 5/1998 |
| WO | WO-9825916 A1 | 6/1998 |
| WO | WO-9832437 A1 | 7/1998 |
| WO | WO-9833499 A1 | 8/1998 |
| WO | WO-9833500 A1 | 8/1998 |
| WO | WO-9949862 A1 | 10/1999 |
| WO | WO-9955898 A1 | 11/1999 |
| WO | WO-9963974 A2 | 12/1999 |
| WO | WO-9965893 A1 | 12/1999 |
| WO | WO-0049009 A1 | 8/2000 |
| WO | WO-0066576 A1 | 11/2000 |
| WO | WO-0117986 A1 | 3/2001 |
| WO | WO-0126651 A2 | 4/2001 |
| WO | WO-0154699 A1 | 8/2001 |
| WO | WO-0202548 A1 | 1/2002 |
| WO | WO-02059113 A1 | 8/2002 |
| WO | WO-03016270 A2 | 2/2003 |
| WO | WO-03035635 A1 | 5/2003 |
| WO | WO-03063859 A1 | 8/2003 |
| WO | WO-03086386 A1 | 10/2003 |
| WO | WO-2004030662 A1 | 4/2004 |
| WO | WO-2005049008 A1 | 6/2005 |
| WO | WO-2006032085 A1 | 3/2006 |
| WO | WO-2006032086 A1 | 3/2006 |
| WO | WO-2008052256 A1 | 5/2008 |
| WO | WO-2008113100 A1 | 9/2008 |
| WO | WO-2010022467 A1 | 3/2010 |
| WO | WO-2010045674 A1 | 4/2010 |
| WO | WO-2012061409 A1 | 5/2012 |
| WO | WO-2012061413 A2 | 5/2012 |

OTHER PUBLICATIONS

Abegaz, et al., Isoflavonoids from the roots of Salsola somalensis. Phytochemistry. 30(4): 1281-4, 1991 (Abstract Only in English).

Agarwal, et al., Isoflavones of two Iris species. Phytochemistry (Elsevier) 23(11):2703-4, 1984. (Abstract Only in English).

(56) References Cited

OTHER PUBLICATIONS

Agarwal, et al., Phenolic constituents of Iris Milesii rhizomes, Phytochemistry (Elsevier) 23(6):1342-3, 1984. (Abstract Only in English).
Aggarwal, et al., From chemoprevention to chemotherapy: common targets and common goals. Expert Opin. Investig. Drugs. 2004;13(10):1327-38.
Akimoto, et al., Genistein, a tyrosine kinase inhibitor, enhanced radiosensitivity in human esophageal cancer cell lines in vitro: possible involvement of inhibition of survival signal transduction pathways. Int. J. Radiation Oncology Biol. Phys. 2001; 50(1):195-201.
Aldrich Handbook of Fine Chemicals and Laboratory Equipment © 2002, Sigma-Aldrich Pty Limited, Australia: Note: Sigma-Aldrich is a US Company, catalogue/handbook from which the pages derive from is the AU publication.
Antus, et al., Synthesis of some pterocarpenes obtained from Brya ebenus, J. Chem. Soc., Perkin Trans. 6:1389-94, 1982 (Abstract Only in English).
Arnone, et al., Isoflavonoid constituents of the West African red wood, *Baphia nitida*. Phtyochemistry. 20(4):799-801, 1981. (Abstract Only in English).
Bartelink et al. The combined use of radiotherapy and chemotherapy in the treatment of solid tumours. Eur J Cancer 38(2):216-222 (2002).
Bellisarii, et al., Tumor necrosis factor-α and cardiovascular diseases. Ital Heart J. 2001;2(6):408-17.
Berge et al. Pharmaceutical Salts. Journal of Pharmaceutical Sciences 66(1):1-19 (Jan. 1977).
Berridge MV, Tan AS. (1998) Trans-plasma membrane electron transport a cellular assay for NADH- and NADPH-oxidase based on extracellular, superoxide-mediated reduction of the sulfonated tetrazolium salt WST-1. Protoplasma. 205:74-82.
Bezuidenhoudt et al., Synthesis of Isoflavanoid Oligomers Using a Pterocarpan as Inceptive Electrophile. J Chem Soc Parkin Trans. 1984; 1:2767-78.
Bradbury, Some oestrogenic 4-phenyl-substituted isoflav-3-ENS, Aust J Chem. 1953;6:447-49.
Briviba, et al., Isoflavonoids as inhibitors of lipid peroxidation and quenchers of singlet oxygen. Antioxidants in Health and Disease, 7(Flavonoids in Health and Disease). 295-302, 1988 (Abstract Only in English).
Bury, et al., Synthesis and pharmacological evaluation of novel cis-3,4-diaryl-hydroxychromanes as high affinity partial agonists for the estrogen receptor. Bioorg Med Chem. 2002;10:125-145.
Caltagirone, et al., Flavanoids apigenin and quercetin inhibit melanoma growth and metastatic potential. Int J Cancer Suppl. 87(4):595-600, 2002. (Abstract Only in English).
PCT/AU2004/001619 International Search Report dated Feb. 2, 2005.
Caltagirone, et al., Interaction with type II estrogen binding sites and antiproliferative activity of tamoxifen and quercetin in human non-small-cell lung cancer, American Journal of Respiratory Cell and Molecular Biology. 17:(1):51-9, 1997. (Abstract Only in English).
Challa, et al. Cyclodextrins in drug delivery: an updated review. AAPS PharmSciTech. Oct. 14, 2005;6(2):E329-357. doi: 10.1208/pt060243.
Constantinou, et al. Phenoxodiol (2H-1-Benzopyran-7-0, 1, 3-(4-hydroxyphenyl), a Novel Isoflavone Derivative, Inhibits DNA Topoisomerase II by Stabilizing the Cleavable Complex. Anticancer Research. 2002;22:2581-86.
Constantinou, et al., Phenoxodiol, a novel isofavone derivative, inhibits dimethylbenz[a]anthracene(DMBA)-induced mammary carcinogenesis in female Sprague—Dawley rats. Eur J Cancer. 2003; 39:1012-18.
De Vincenzo, et al.,Flavanoids and negative control of cell proliferation in ovarian tumors. Acta Medica Romana. 30(1-2):126-32, 1992. (Abstract Only in English).

Dorai, et al , Role of chemopreventive agents in cancer therapy. Cancer Lett. 215:129-40, 2004.
Fukui, et al., The synthesis of irisolone, Bull. Chem. Soc. Japan. 38(6):887-93, 1965 (Abstract Only in English).
Gamble, et al., Phenoxodiol, an experimental anticancer drug, shows potent antiangiogenic properties in addition to its antitumour effects. Int. J. Cancer. 118:2412-20, 2006.
Giacomelli et al., Silybin and its bioavailable, phospholipid complex(IdB 1016) potentiate in vitro and in vivo the activity of cisplatin. Life Sciences. Feb. 8, 2002; 70(12):1447-59 (Abstract Only in English).
Gupta et al., The use of Friedel-Crafts reactions for the synthesis of deoxybenzoins. Indian J Chem. 1968; 6(9):481-4 (Abstract Only in English).
Hem Chandra Jha, et al., Carbon-13—chemical shift assignments of chromones and isoflavones. Can J Chem. 58:1211-19, 1980.
Hersey, et al., How melanoma cells evade trail-induced apoptosis. Nat Rev Cancer. Nov. 2001; 1(2)142-50.
Horie, et al.,Studies of the selective O-alkylation and dealkylation of flavonoids. XX. A convenient method for synthesizing 5,6,7-trihydroxyisoflavones and 5,6-dihydroxy-7-methoxyisoflavones. Pharm Bull. 44(3):486-91, 1996. (Abstract Only in English).
Hu et al., Identification of CYP1A2 as the main isoform for the Phase 1 hydroxylated metabolism of genistein and a prodrug converting exzyme of methylated isoflavones. Drug Metabolism and Dispostion, 31(7):924-931, 2003.
Ito, et al., Isoflavonoids from Belamcanda chinensis. Pharm Bull. 49(9):1229-31, 2001 (Abstract Only in English).
Kakeji, et al., Preclinical studies of the combination of angiogenic inhibitors with cytotoxic agents. Invest New Drugs. 15:39-48, 1997.
Kamsteeg, et al., Phenoxodiol—an isoflavone analog—induces apoptosis in chemoresistant ovarian cancer cells. Oncogene. 22:2611-20, 2003.
Kang, et al., "Scientific Analysis of Formulation Theory of Chungpesagan-tang; In vitro Cytotoxicity of Cisplatin Combined with Chungpesagan-tang", Natural Product Sciences, vol. 6(4), pp. 165-169, 2000.
Kanzawa, et al., Evaluation of synergism by a novel three-dimensional model for the combined action of cisplatin and etoposide on the growth of a human small-cell lung-cancer cell line, SBC-3. Int. J. Cancer 71, 311-319, 1997.
Khoshyomn, et al., Synergistic Action of Genistein and Ciplatin on Growth Inhibition and Cytotoxicity of Human Medulloblastoma Cells. Pediatr Neurosurg. 33:123-31, 2000.
Kinjo, et al., Novel santalin analogs from *Pterpcarpus santalinus* (leguminosae): their biogenesis and anti-oxidative activities. Tennen Yuki Kagobutsu Toronkai Koen Yoshishu. 37:493-8, 1995. (Abstract Only in English).
Klus, et al., Formation of polyhydroxylated isoflavones from the soybean seed isoflavones daidzein and glycitein by bacteria isolated from tempe. Arch Microbiol. 164(6):428-34, 1995 (Abstract Only in English).
Kothari, et al. Inhibition of cholesterol ester transfer protein by CGS 25159 and changes in lipoproteins in hamsters: Atherosclerosis. (Shannon, Ireland) 128(1):59-66, 1997.
Kulling, et al., Oxidative metabolism of the soy isoflavones daidzein and genistein in humans in vitro and in vivo. J Agric Food Chem. 2001; 49(6):3024-33 (Abstract Only in English).
Lawson, Estrogenic activity of some derivatives of isoflaven and isoflavanol. J Chem Soc. 4448-50, 1954 (Abstract Only in English).
Lei, et al., Enhancement of Chemosensitivity and Programmed Cell death by Tyrosine Kinase Inhibitors Correlates with EGFR Expression in Non-Small Cell Lung Cancer Cells. Anticancer Res. 19:221-28, 1989.
Li, et al., Apoptosis-Inducing Effect of Chemotherapeutic Agents Is Potentiated by Soy Isoflavone Genistein, a Natural Inhibitor of NF-KB in BxPC-3 Pancreatic Cancer Cell Line. Pancreas. (28)4:e90-5, 2004.
Mani, et al., Isoflavones. I. Bromination of isoflavones. J Inst Chem. 1974; 46(Pt.3):61-5 (Abstract Only in English).
Mani, et al, Isoflavones. III. Nitration of 7,8- and 6,7-dihydroxyisoflavones and their methyl ether. J Inst Chem. 1971; 43(6):234-40 (Abstract Only in English).

(56) References Cited

OTHER PUBLICATIONS

Mansour, et al., Enhancement of Chemotherapeutic Efficacy by Combining Agents that Block IL-10 in CLL Cell Lines. New Jersey Medical School, UMDNJ, Newark, NJ, USA Blood. Nov. 16, 2002; 100(11) Abstract No. 4997. Print (Abstract Only in English).
McDonnell, et al., Improvement in Efficacy of Chemoradiotherapy by Addition of and Antiangiogenic Agent in a Murine Tumor Model. J Surg Res. 2004; 116:19-23.
Micheli, et al., "Coumestro, Plant Phenolics, and Synthetic Estrogens: a Correlation of Structure and Activity", Journal of Medicinal and Pharmaceutical Chemistry, vol. 5, 1962, pp. 321-335.
Montandon, et al., In-vitro versus in-vivo activities of new 5-lipoxygenase inhibitors with anti-inflammatory activity, Int J Tissue React. 1989; 11(3); 107-12 (Abstract Only in English).
Nakata et al., C225 Antiepidermal Growth Factor Receptor Antibody Enhances the Efficacy of Docetaxel Chemoradiotherapy. Int J Radiation Oncology Biol Phys. 2004; 59(4): 1163-73.
Neelam, et al., Combination of flavone acetic acid (FAA) with adriamycin, cis-platinum and diflouoromethylornithine (DFMO) in vitro against human colon cancer cells. Invest New Drugs. Aug. 1990; 8(3):263-8 (Abstract Only in English).
O'Dwyer, et al., Antitumor Activity and Biochemical Effects of Aphidicolin Glycinate(NSC 303812) Alone and in Combination with Cisplatin in Vivo. Cancer Res. Feb. 1, 1994; 54:724-29.
O'Neill, et al., Inducible Isoflavonoids from the Lima Bean, Phaseolus Lunatus. Phytochemistry. 1986; 25(6): 1315-22.
PCT/AU2005/001435 International Search Report dated Dec. 21, 2005.
PCT/AU2005/001436 International Search Report dated Dec. 21, 2005.
PCT/US2011/058815 International Preliminary Report on Patentability dated May 7, 2013.
PCT/US2011/058815 International Search Report and Written Opinion dated Mar. 12, 2012.
PCT/US2011/058820 International Preliminary Report on Patentability dated May 8, 2013.
PCT/US2011/058820 Search Report and Written Opinion dated Jun. 21, 2012.
Rafi, et al., Modulation of bcl-2 and Cytotoxicity by Licochalcone-A, a Novel Estrogenic Flavonoid. Anticancer Res. 20:2653-58, 2000.
Ravindranath, et al., Anticancer Therapeutic Potential of Soy Isoflavone, Genistein. Complementary and Alternative Approaches to Biomedicine, edited by Edwin L. Cooper and Nobuo Yamaguchi. Kluwer Academic/Plenum Publishers. p. 121, 2004.
Registration No. 1157-39-7, 4H-1-Benzopyran-4-one, 7-methoxy-3-(4-methoxyphenyl)-methyl- (9CI), Nov. 16, 1984.
Registration No. 116703-40-3, 4H-1-Benzopyran-4-one, 2,3-dihydro-7,8-dimethoxy-3-(4-methoxyphenyl)-(9CI), Oct. 2, 1988.
Registration No. 116703-49-2, 4H-1-Benzopyran-4-one, 2,3-dihydro-7,8-dihydroxy-3-(4-methoxyphenyl)-(9CI), Oct. 2, 1988.
Registration No. 116718-51-5, 4H-1-Benzopyran-4-one, 7-hydroxy-3-(4-methoxyphenyl)-8-methyl-methyl-(9CI), Oct. 2, 1988.
Registration No. 124093-18-1, 4H-1-Benzopyran-4-one, 2,3-dihydro-7-hydroxy-3-(4-hydroxy-3-methoxyphenyl)-(9CI), Dec. 1, 1989.
Registration No. 129159-04-2, 4H-1-Benzopyran-4-one, 2,3-dihydro-3-(4-hydroxyphenyl)-(9CI), Aug. 31, 1990.
Registration No. 129159-05-3, 4H-1-Benzopyran-4-one, 3-(3,4-dihydroxyphenyl)-2,3-dihydro-(9CI), Aug. 31, 1990.
Registration No. 13139-86-1, Magnesium, bromo(4-methoxyphenyl)-(9CI), Nov. 16, 1984.
Registration No. 142050-44-0, 4H-1-Benzopyran-4-one, 7-hydroxy-3-[4-methoxy-3-(methoxy-t3)phenyl]-(9CI), Jun. 26, 1992.
Registration No. 143358-24-1, 4H-1-Benzopyran-4-one, 2,3-dihydro-7-methoxy-3-(4-methoxyphenyl)-(+)-(9CI), Sep. 9, 1992.
Registration No. 143358-39-8, 4H-1-Benzopyran-4-one, 2,3-dihydro-7-methoxy-3-(4-methoxyphenyl)-(-) (9CI), Sep. 9, 1992.
Registration No. 15236-11-0, 4H-1-Benzopyran-4-one, 2,3-dihydro-7-methoxy-3-(4-methoxyphenyl)-(9CI), Nov. 16, 1984.
Registration No. 16750-63-3, Magnesium, bromo(2-methoxyphenyl)-(9CI), Nov. 16, 1984.
Registration No. 201678-33-3, 4H-1-Benzopyran-4-one, 3-(3,4-dimethoxyphenyl) -2,3-dihydro-7,8-dimethoxy-(9CI), Feb. 22, 1998.
Registration No. 206257-38-7, 4H-1-Benzopyran-4-one, 2, 3-dihydro-3-(4-hydroxyphenyl)-7-methoxy-(9CI), Jun. 3, 1998.
Registration No. 24160-14-3 , 4H-1-Benzopyran-4-one, 3-(3,4-dimethoxyphenyl)-7-hydroxy-(9CI), Nov. 16, 1984.
Registration No. 288267-24-3, 4H-1-Benzopyran-4-one, 7-hydroxy-3-(4-hydroxy-3-methoxyphenyl)-8-methyl-(9CI), Sep. 6, 2000.
Registration No. 304892-19-1, 4H-1-Benzopyran-4-one, 3-(3,4-dihydroxyphenyl)-2,3-dihydro-7-hydroxy-(9CI), Nov. 29, 2000.
Registration No. 36282-40-3, Magnesium, bromo(3-methoxyphenyl)-, Nov. 16, 1984.
Registration No. 39604-72-3, 4H-1-Benzopyran-4-one, 2,3-dihydro-7methoxy-3-(4-methoxyphenyl)-8-methyl-(9CI), Nov. 16, 1984.
Registration No. 4626-22-6, 4H-1-Benzopyran-4-one, 2,3-dihydro-7-hydroxy-3-(4- methoxyphenyl)-(9CI), Nov. 16, 1984.
Registration No. 67492-31-3, 4H-1-Benzopyran-4-one, 2,3-dihydro-7-hydroxy-3-(3-hydroxy-4-methoxyphenyl)-(9CI), Nov. 16, 1984.
Registration No. 680195-83-9, 4H-1-Benzopyran-4-one, 2,3-dihydro-7,8-dihydroxy-3-(4-hydroxyphenyl)-(9CI), May 6, 2004.
Registration No. 83206-83-1, 4H-1-Benzopyran-4-one, 3-(3,4-dimethoxyphenyl)-2,3-dihydro-7-hydroxy-(9CI), Nov. 16, 1984.
Registration No. 85915-64-6, 2H-1-Benzopyran-7-ol, 4-[5-(3,4-dihydro-7-hydroxy-2-H-1-benzopyran-3-yl)-4-hydroxy-2-methoxyphenyl]-3,4-dihydro-3-(2-hydroxy-4-methoxyphenyl)-,[3S-[3 -4β(R*)]]-(9CI), Nov. 16, 1984.
Registration No. 85915-66-8, 2H-1-Benzopyran, 4-[5-(3,4-dihydro-7-methoxy-2H-1-benzopyran-3-y1)-2,4-dimethoxypheny1]-3-(2,4-dimethoxypheny1)-3,4-dihydro-7-methoxy-, [3S-[3α4β(R*)]]-(9CI), Nov. 16, 1984.
Registration No. 95307-73-6, 4H1-Benzopyran-4-one-2-d, 2,3-dihydro-2-d-7-hydroxy-3-(4-methoxyphenyl)-(9CI), Mar. 16, 1985.
Registration No. 95457-39-9, 4H-1-Benzopyran-4-one-4-14C, 3-(3,4-dimethoxyphenyl)-7-hydroxy-(9CI), Mar. 23, 1985.
Registration No. 95541-42-7, 1,3-Benzenediol, 4-[3,4-dihydro-3-(2-hydroxy-4-methoxypheny1)-7-methoxy-2H-1-benzopyran-4-yl]-,(3R-trans)-(9CI), Mar. 30, 1985.
Registration No. 95541-43-8, 2H-Benzopyran, 3,4-bis(2,4-dimethoxyphenyl)-3,4-dihydro-7-methoxy-,(3R-trans)-(9CI), Mar. 30, 1985.
Registration No. 95541-44-9, 1,3,5-Benzenetriol,2-[3,4-dihydro-3-(2-hydroxy-4-methoxypheny1)-7-methoxy-2H-1-benzopyran-4-yl)-, (3R-trans)-(9CI) (1984).
Registration No. 95541-45-0, 1,3,5-Benzenetriol,2,4-bis[3,4-dihydro-3-(2-hydroxy-4-methoxypheny1)-7-methoxy-2H-1-benzopyran-4-yl]-,[3R-[3α,4α(3R*,4S"])-(9CI) (1984).
Registration No. 95541-46-1, 2H-1-Benzopyran,3-(2,4-dimethoxyphyeny1)-3,4-dihydro-7-methoxy-4(2,4,6-trimethoxyphenyl)-, (3R-trans)-(9CI) (1984).
Registration No. 95541-51-8, 2H-1-Benzopyran-7-ol, 3-[3,4-dihydro-3-(2-hydroxy-4-methoxypheny1)-7-methoxy-2H-1-benzopyran-4-y1]-2-hydroxy-4-methoxypheny1]-3,4-dihydro-,[3R-3α,4β(S*)]]-(9CI) (1984).
Registration No. 95541-53-0, 2H-1-Benzopyran, 4-[5(3,4-dihyrdro-7-methoxy-2H-1-benzopyran-3-y1)-2,4-dimethoxypheny1]-3-(2,4-dimethoxypheny1)-3,4-dihydro-7-methoxy-,[3R-[3α,4β(S*)]]-(9CI) (1984).
Registration No. 95541-54-1, 2H-1-Benzopyran-7-ol, 3-[-[4-dihydro-4-[4-hydroxy-5-(7-hydroxy-2H-1-benzopyran-3-y1)-2-methoxypheny1]-3-(2-hydroxy-4-methon/pheny1)-(3S-trans)-(9CI) (1984).
Registration No. 95541-57-4, 2H-1-Benzopyran,4-[2,4-dimethoxy-5-(7-methoxy-2H-1-benzopyran-3-yl)phenyl]-3-(2,4-dimethoxyphenyl)-3,4-dihydro-7-methoxy-,(3S-trans)-(9CI) (1984).
Registration No. 95541-66-5, 2H-1-Benzopyran, 4-(2,4-dimethoxypheny1)-3,4-dihydro-7-methoxy-3-[4-methoxy-2-(methoxymethoxy)phenyl]-,(3R-trans)-(9CI) (1984).
Registration No. 95762-78-0, 2H-1-Benzopyran,4,4'-(2,4,6-trimethoxy-1,3-phenylene)bix[3-(2,4-dimethoxyphenyl)-3,4-dihydro-7-methoxy-,[3R[3α,4β(3'R*,4'S*)]-(9CI) (1984).

(56) References Cited

OTHER PUBLICATIONS

Scambia, et al., Antiproliferative effect of silybin on gynaecological malignancies;synergism with cisplatin and doxorubicin. Eur J Cancer. May 1996; 32A(5):877-82 (Abstract Only in English).
Scambia, G. Synergistic antiproliferative activity of quercetin and cisplatin on ovarian cancer cell growth. Anti-Cancer Drugs Oct. 1990; 1(1):45-8 (Abstract Only in English).
Sepulveda-Boza, et al., The preparation of new isoflavones, Synthetic Communications. 2001; 3(12):1933-40.
Szlosarek, et al., Tumour necrosis factor a: a potential target for the therapy of solid tumours. The Lancet Oncology. Sep. 2003; 4:565-73.
Tamura, et al., Genistein Enhances the Cisplatin-Induced Inhibition of Cell Growth and Apoptosis in Human Malignant Melanoma Cells. Pigment Cell Res. 2003; 16:470-76 (Abstract Only in English).
Teo, et al., Synthesis of 3-(p-fluorophenyl)-4-arylchrom-3-enes as selective ligands for antiestrogen-binding sites. J Chem Res. Synopses. 1990; 1:4-5 (Abstract Only in English).
Teo, et al., Synthesis of arylchromenes and arylchromans. Bulletin of the Singapore National Institute of Chemistry. 1994; 22:69-74 (Abstract Only in English).
Therasse et al., New guidelines to evaluate the response to treatment in solid tumors: European Organization for Research and Treatment of Cancer, National Cancer Institute of the United States, National Cancer Institute of Canada. J Natl Cancer Inst 92:205-216 (2000).
Todorov, et al., Role of a proteolysis-inducing factor(PIF) in a cachexia induced by a human melanoma(G361). Br J Cancer. 1999; 80(11):1734-37.
Tubiana. The combination of radiotherapy and chemotherapy: a review. Int J Radiat Biol 55(4):497-511 (1989).
U.S. Appl. No. 11/230,726 Office Action dated Jan. 22, 2007.
U.S. Appl. No. 11/230,726 Office Action dated Mar. 4, 2008.
U.S. Appl. No. 11/230,726 Office Action dated Oct. 28, 2008.
U.S. Appl. No. 13/891,975 Office Action dated Apr. 23, 2014.
U.S. Appl. No. 11/230,505 Office Action dated Dec. 17, 2009.
U.S. Appl. No. 11/230,505 Office Action dated Jun. 9, 2008.
U.S. Appl. No. 11/230,505 Office Action dated Mar. 12, 2009.
U.S. Appl. No. 11/230,505 Office Action dated Sep. 4, 2007.
U.S. Appl. No. 11/230,726 Office Action dated Aug. 10, 2007.
U.S. Appl. No. 12/551,277 Office Action dated Jan. 6, 2011.
U.S. Appl. No. 12/551,277 Office Action dated May 28, 2010.
U.S. Appl. No. 13/293,947 Office Action dated Jul. 20, 2012.
U.S. Appl. No. 13/293,947 Office Action dated May 24, 2013.
U.S. Appl. No. 13/293,947 Office Action dated Nov. 8, 2012.
U.S. Appl. No. 13/415,697 Office Action dated Jul. 6, 2012.
U.S. Appl. No. 13/881,609 Office Action dated Apr. 10, 2015.
U.S. Appl. No. 13/881,609 Office Action dated Aug. 7, 2015.
U.S. Appl. No. 13/881,609 Office Action dated May 16, 2016.
U.S. Appl. No. 14/186,940 Office Action dated Aug. 6, 2014.
U.S. Appl. No. 14/186,940 Office Action dated Nov. 21, 2014.
U.S. Appl. No. 14/922,472 Office Action dated Sep. 26, 2016.
U.S. Appl. No. 15/175,386 Office Action dated Oct. 6, 2017.
U.S. Appl. No. 15/456,182 Office Action dated Nov. 20, 2017.
U.S. Appl. No. 15/622,569 Office Action dated Sep. 7, 2017.
U.S. Appl. No. 15/961,259 Office Action dated Sep. 5, 2018.
U.S. Appl. No. 16/129,589 Final Office Action dated Nov. 7, 2019.
U.S. Appl. No. 16/129,589 Office Action dated Apr. 18, 2019.
U.S. Appl. No. 16/129,589 Office Action dated Mar. 19, 2020.
U.S. Appl. No. 16/444,981 Final Office Action dated Aug. 20, 2020.
U.S. Appl. No. 16/444,981 Office Action dated Mar. 3, 2020.
U.S. Appl. No. 17/193,335 Office Action dated Sep. 15, 2022.
Varady, J. The flavonoids of Podocarpus spicatus. I. Structure of podospicatin. Synthesis of podospicatin mono-,di-, and trimethyl ethers. Periodica Polytech. 1963; 7(4):241-58 (Abstract Only in English).
Verma et al., Smooth Conversion of 3,4-Diarylcoumarins and 3,4,5-Triaryl-2(5H)-furanones to 2H-Chromene and 2,5-Dihydrofuran Derivatives with Dimethyl Sulfide-Borane Complex. Synthesis. 1988; 1:68-70.
Voss, C. et al., New isoflavonoids as inhibitors of porcine 5-lipoxygenase. Biochem Pharmacol. 1992; 44(1):157-62 (Abstract Only in English).
Waud, et al., Antitumor drug cross-resistance in vivo in a cisplatin-resistant murine P388 leukemia, Cancer Chemotherapy and Pharmacology. 1991; 27 (6):456-63 (Abstract Only in English).
Weidenborner, et al., Control of storage fungi of the genus *Aspergillus* on legumes with flavonoids and isoflavonoids. Angewandte Botanik. 1990: 64(1-2):175-90 (Abstract Only in English).
Wolfbeis, et al., The Absorption and Fluorescence of Isoflavones and the Effect of Shift Reagents. Z Naturforsch. 39b:238-43, 1984.
Zyner, et al., Platinum(II) and palladium(II) N,0-Chelates with substituted flavanone containing ligangs. Acta Pol Pharm. 1999; 56(2): 159-67.
Zyner, et al., Pt(II) and Pt(II) complexes of 3-aminoflavone: In vitro and in vivo evaluation. Pharmazie. 1999; 54(12):945-46.
U.S. Appl. No. 13/881,599 Office Action dated Apr. 9, 2015.
U.S. Appl. No. 13/881,599 Office Action dated Aug. 18, 2016.
U.S. Appl. No. 15/175,386 Office Action dated May 10, 2018.
Co-pending U.S. Appl. No. 17/193,335, filed Mar. 5, 2021.
European Patent Application No. 05779877.9 European Search Report dated Apr. 28, 2009.
European Patent Application No. 05787045.3 European Search Report dated Oct. 20, 2008.
European Patent Application No. 11180383.9 European Search Report dated Jul. 13, 2012.
European Patent Application No. 11175917.1 European Search Report dated Dec. 16, 2011.
Japanese Patent Application No. 2013-536929 First Office Action dated Aug. 25, 2015 (with English language translation).

\* cited by examiner

ISOFLAVONOID COMPOUNDS AND METHODS FOR THE TREATMENT OF CANCER

CROSS-REFERENCE

This application is a continuation of U.S. patent application Ser. No. 18/154,267, filed Jan. 13, 2023, which is a continuation of U.S. patent application Ser. No. 17/023,681, filed Sep. 17, 2020, now U.S. Pat. No. 11,583,514, issued Feb. 21, 2023, which is a continuation of U.S. patent application Ser. No. 16/129,589, filed Sep. 12, 2018, now abandoned, which is a continuation of U.S. patent application Ser. No. 15/456,182, filed Mar. 10, 2017, now U.S. Pat. No. 10,105,346, issued Oct. 23, 2018, which is a continuation of U.S. patent application Ser. No. 13/881,609, filed Apr. 16, 2014, now U.S. Pat. No. 9,663,484, issued May 30, 2017, which was filed pursuant to 35 U.S.C. § 371 as a United States National Phase Application of International Application Ser. No. PCT/US2011/058815, filed Nov. 1, 2011, which claims the benefit of priority to U.S. Provisional Application No. 61/408,972, filed Nov. 1, 2010, all of which are incorporated herein by reference in their entirety.

BACKGROUND OF THE INVENTION

Cancer is the leading cause of death worldwide.

SUMMARY OF THE INVENTION

Provided herein, in some embodiments, is a pharmaceutical composition comprising a compound of formula II or a pharmaceutically acceptable salt thereof:

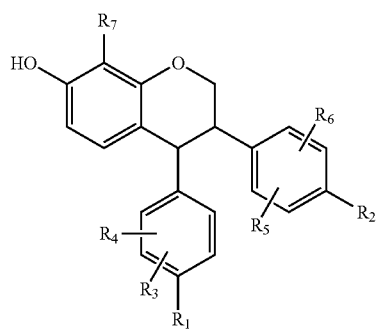

Formula (II)

wherein
$R_1$ is hydroxy, alkoxy, haloalkyl, or halo;
$R_2$ is hydroxy or alkoxy;
$R_3$ is alkyl, halo, or haloalkyl;
$R_4$, $R_5$, and $R_6$ are independently hydrogen, hydroxy, alkoxy, halo, haloalkyl, or alkyl; and
$R_7$ is alkyl or hydrogen.

In some embodiments, the pharmaceutical composition comprises a compound (i.e., isoflavonoid derivative) of formula II, wherein $R_1$ is hydroxy or methoxy. In other embodiments, $R_1$ is hydroxy. In other embodiments, $R_1$ is methoxy. In other embodiments, $R_1$ is halo. In other embodiments, $R_1$ is fluoro. In other embodiments, $R_2$ is hydroxy. In other embodiments, $R_3$ is methyl. In other embodiments, $R_3$ is fluoro. In other embodiments, $R_7$ is methyl.

Also provided herein, in some embodiments, is a pharmaceutical composition comprising a compound of formula III or a pharmaceutically acceptable salt thereof:

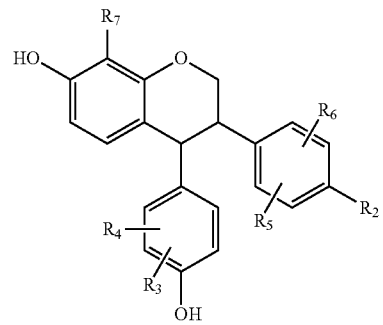

Formula (III)

wherein
$R_2$ is hydroxy or alkoxy;
$R_3$, $R_4$, $R_5$, and $R_6$ are independently hydrogen, hydroxy, alkoxy, halo, haloalkyl or alkyl; and
$R_7$ is alkyl.

In some embodiments, the pharmaceutical composition comprises a compound (i.e., isoflavonoid derivative) of formula III, wherein $R_2$ is hydroxy. In other embodiments, $R_3$ is hydrogen or alkyl. In specific embodiments, $R_3$ is hydrogen. In specific embodiments, $R_3$ is alkyl. In other embodiments, $R_3$ is $C_{1-6}$alkyl. In other embodiments, $R_3$ is $C_{1-3}$alkyl. In further or additional embodiments, $R_3$ is methyl. In other embodiments, $R_3$ is haloalkyl. In other embodiments, $R_7$ is methyl.

Some embodiments provided herein describe a pharmaceutical composition comprising a compound of formula IV or a pharmaceutically acceptable salt thereof:

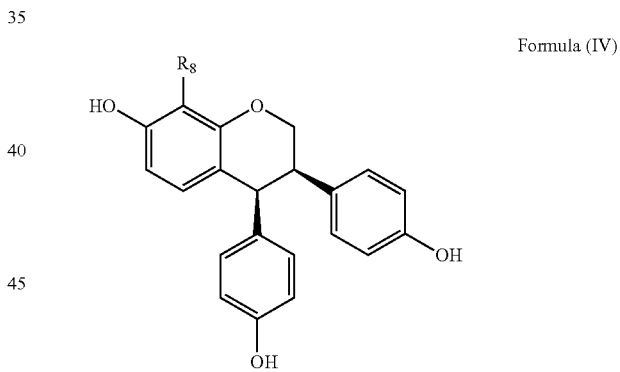

Formula (IV)

wherein
$R_8$ is hydrogen or alkyl.

In some embodiments, the pharmaceutical composition comprises a compound (i.e., isoflavonoid derivative) of formula IV, wherein $R_8$ is hydrogen. In other embodiments, $R_8$ is $C_{1-6}$alkyl. In other embodiments, $R_8$ is $C_{1-3}$alkyl. In other embodiments, $R_8$ is methyl. In other embodiments, $R_8$ is ethyl. In other embodiments, $R_8$ is propyl. In other embodiments, $R_8$ is isopropyl.

In some embodiments, the composition comprising a compound of formula II, III or IV further comprises an anti-cancer agent selected from the group consisting of cisplatin, carboplatin, paclitaxel, gemcitabine, doxorubicin, epirubicin, cyclophosphamide, capecitabine, 5-fluorouracil, vinorelbine, trastuzumab or bevacizumab. In specific embodiments, the pharmaceutical composition further comprises carboplatin.

Also described herein is a compound of formula II, III, or IV for use in inducing apoptosis in a cancer cell. In some embodiments, the type of cancer cell apoptosed, or otherwise targeted according to any method described herein, is selected from the group consisting of bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer and cancers of the brain. In certain embodiments, the type of cancer cell is human breast, prostate, ovarian, pancreatic, or cervical cancer. In certain specific embodiments, the type of cancer cell is human breast cancer or ovarian cancer.

In some embodiments, any method described herein further comprises administering, e.g., to a targeted cell, a chemotherapeutic agent. In specific embodiments, the chemotherapeutic agent is selected from the group consisting of cisplatin, carboplatin, paclitaxel, gemcitabine or doxorubicin.

In certain embodiments, a cancer cell apoptosed, or otherwise targeted according to any method described herein, is present in an individual. In specific embodiments, the individual is in need of cancer therapy. In certain specific embodiments, the composition is administered to the individual intravenously.

Also described herein is a compound of formula II, III, or IV for use in the treatment of cancer in an individual in need of cancer therapy.

Some embodiments provided herein describe a compound of formula II, III, or IV for use in increasing, inducing, or restoring sensitivity of a cancer cell to a chemotherapeutic agent, anti-cancer agent or radiation therapy. In some embodiments, the cancer cell has lost sensitivity to a chemotherapeutic agent, anti-cancer agent or radiation therapy.

In some embodiments, the type of cancer cell or cancer sensitized according to a method described herein is bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer or a cancer of the brain. In certain embodiments, the type of cancer cell is human breast, prostate, ovarian, pancreatic, or cervical cancer. In certain specific embodiments, the type of cancer cell is human breast cancer or ovarian cancer. In more specific embodiments, the cancer cell is a human breast cancer cell. In other specific embodiments, the cancer cell is a human ovarian cancer cell.

In certain embodiments, the cancer cell sensitized according to a method described herein is present in an individual. In specific embodiments, the individual is in need of cancer therapy. In certain specific embodiments, the composition is administered to the individual intravenously. In some embodiments, the cancer cell has lost sensitivity to a chemotherapeutic agent or radiation therapy.

Some embodiments provided herein describe a kit comprising a compound of formula II, III, or IV. In some embodiments, the kit provided herein has a sealable, plastic infusion bag. In some embodiments, the kit further comprises intravenous tubing. In other embodiments, the kit further comprises a needle.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

There is a continuing need to develop and provide effective therapies for the treatment of cancer. Described herein is a composition that has anti-cancer activity. The composition described herein comprises isoflavonoid derivatives (substituted diaryl chroman derivatives). Also provided herein are methods to induce apoptosis in a cancer cell, methods to treat cancer in individuals in need of cancer therapy, and methods to increase sensitivity of a cancer cell to a chemotherapeutic agent and/or radiation therapy (or to sensitize an individual to a particular chemotherapy).

Certain Definitions

Unless otherwise noted, terminology used herein should be given its normal meaning as understood by one of skill in the art.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The terms "$C_1$-$C_3$-alkyl" and "$C_1$-$C_6$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$-$C_3$-alkyl radicals include methyl, ethyl, propyl and isopropyl. Examples of $C_1$-$C_6$-alkyl radicals include, but not limited to, methyl, ethyl, propyl, isopropyl, n-butyl, tert-butyl, neopentyl and n-hexyl.

The term "cycloalkyl" as used herein refers to a monovalent group derived from a monocyclic or bicyclic saturated carbocyclic ring compound containing between three and twenty carbon atoms by removal of a single hydrogen atom.

The term "$C_3$-$C_6$ cycloalkyl" denoted a monovalent group derived from a monocyclic or bicyclic saturated carbocyclic ring compound by removal of a single hydrogen atom. Examples include cyclopropyl, cyclobutyl, cyclopentyl, cyclohexyl.

The alkyl group or cycloalkyl group may optionally be substituted by one or more of fluorine, chlorine, bromine, iodine, carboxyl, $C_{1-4}$ alkoxycarbonyl, $C_{1-4}$ alkylaminocarbonyl, di-($C_{1-4}$ alkyl)-aminocarbonyl, hydroxyl, $C_{1-4}$ alkoxy, formyloxy, $C_{1-4}$ alkylcarbonyloxy, $C_{1-4}$ alkylthio, $C_{3-6}$ cycloalkyl or phenyl.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The terms "$C_1$-$C_3$-alkoxy", "$C_1$-$C_6$-alkoxy" as used herein refers to the $C_1$-$C_3$-alkyl group and $C_1$-$C_6$-alkyl group, as previously defined, attached to the parent molecular moiety through an oxygen atom. Examples of $C_1$-$C_6$-alkoxy radicals include, but not limited to, methoxy, ethoxy, propoxy, isopropoxy, n-butoxy, tert-butoxy, neopentoxy and n-hexoxy.

The term "halo" and "halogen" as used herein refer to an atom selected from fluorine, chlorine, bromine and iodine.

The term "haloalkyl" includes "alkyl" wherein one or more such as 1, 2, 3, 4, or 5 of the hydrogens have been replaced by a halo atom. The haloalkyl may be straight chain or branched chain "alkyl" unit. Non-limiting examples include —$CH_2F$, —$CHF_2$, —$CF_3$, —$CH_2CH_2F$, —$CH_2CHF_2$, —$CH_2CF_3$, —$CF_2CH_2F$, —$CF_2CHF_2$, —$CF_2CF_3$, —$CH_2Cl$, —$CHCl_2$, —$CCl_3$, —$CH_2Br$, —$CHBr_2$, and —$CBr_3$.

The term "fluoroalkyl" includes "alkyl" wherein one or more such as 1, 2, 3, 4, or 5 of the hydrogens have been replaced by fluoro. The fluoroalkyl may be straight chain or branched chain "alkyl" unit. Preferred fluoroalkyl groups include trifluoromethyl and pentafluoroethyl.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. For example, S. M. Berge, et al. describes pharmaceutically acceptable salts in detail in J. Pharmaceutical Sciences, 66: 1-19 (1977), incorporated herein by reference for this purpose. The salts are prepared in situ during the final isolation and purification of the compounds described herein, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "cyclodextrin," as used herein, refers to cyclic carbohydrates consisting of at least six to eight sugar molecules in a ring formation. The outer part of the ring contains water soluble groups; at the center of the ring is a relatively nonpolar cavity able to accommodate small molecules.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. An appropriate "effective" amount in any individual case may be determined using techniques, such as a dose escalation study.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease).

The term "carrier" as used herein, refers to relatively nontoxic chemical compounds or agents that facilitate the incorporation of a compound into cells or tissues.

Compounds

Some embodiments of the present invention describe a pharmaceutical composition comprising a compound (i.e., isoflavonoid derivative) of general formula I:

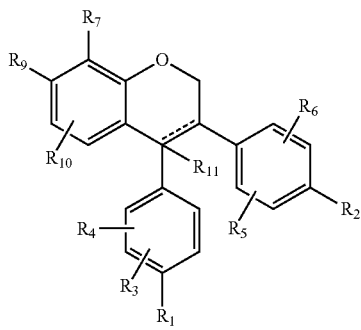

Formula (I)

wherein $R_1$ is hydrogen, hydroxy, halo, $NR_{14}R_{15}$, $C_{3-6}$cycloalkyl, $C_{1-6}$alkoxy, $C_{1-6}$haloalkyl, $C_{2-6}$alkenyl, $COOR_{12}$, $COR_{13}$, $(O)_nC_{1-4}$alkylene$NR_{14}R_{15}$ or $C_{1-6}$alkyl optionally substituted by one or more hydroxy, chloro, bromo, iodo or $NR_{14}R_{15}$ groups;

$R_2$, $R_3$, $R_4$, $R_5$, $R_6$, $R_9$, and $R_{10}$ are independently hydrogen, hydroxy, halo, $NR_{14}R_{15}$, $C_{3-6}$cycloalkyl, $C_{1-6}$alkoxy, $C_{1-6}$haloalkyl, $C_{2-6}$alkenyl, $COOR_{12}$, $COR_{13}$, or $C_{1-6}$alkyl optionally substituted by one or more hydroxy, chloro, bromo, iodo or $NR_{14}R_{15}$ groups;

$R_7$ is hydrogen, hydroxy, halo, $NR_{14}R_{15}$, $C_{3-6}$cycloalkyl, $C_{1-6}$alkoxy, $C_{2-6}$alkenyl, $C_{1-6}$haloalkyl or $C_{1-6}$alkyl optionally substituted by one or more hydroxy, chloro, bromo, iodo or $NR_{14}R_{15}$ groups;

the drawing ==== and $R_2$ together represent a double bond or the drawing ==== represents a single bond and $R_{11}$ is hydrogen, hydroxy, $NR_{14}R_{15}$, $C_{1-3}$alkoxy, $C_{1-3}$fluoroalkyl, halo or $C_{1-3}$alkyl optionally substituted by one or more hydroxy, chloro, bromo, iodo or $NR_{14}R_{15}$ groups;

$R_{11}$ and $R_{12}$ are independently hydrogen, $C_{1-6}$alkyl, $C_{3-6}$cycloalkyl, or trialkyl silyl;

$R_{13}$ is hydrogen, $C_{1-6}$alkyl, $C_{3-6}$cycloalkyl or $NR_{14}R_{15}$;

n represents 0 or 1; and $R_{14}$ and $R_{15}$ independently represent hydrogen or $C_{1-6}$alkyl or $NR_{14}R_{15}$ when taken together represents a 5 or 6 membered heteroaromatic or heterocyclic, or a pharmaceutically acceptable salt thereof.

In some embodiments, the pharmaceutical composition comprises a compound (i.e., isoflavonoid derivative) of formula II:

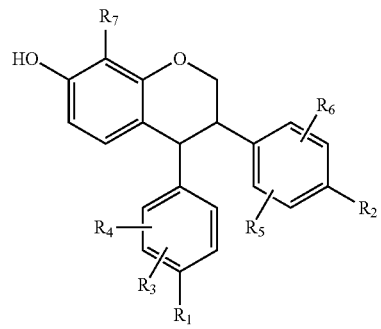

Formula (II)

$R_1$ is hydroxy, alkoxy, haloalkyl, or halo;
$R_2$ is hydroxy or alkoxy;
$R_3$ is alkyl, halo, or haloalkyl;
$R_4$, $R_5$, and $R_6$ are independently hydrogen, hydroxy, alkoxy, halo, haloalkyl, or alkyl; and
$R_7$ is alkyl or hydrogen;
or a pharmaceutically acceptable salt thereof.

Some embodiments provided herein describe a compound of Formula II that has a structure of Formula (II-a) or (II-b):

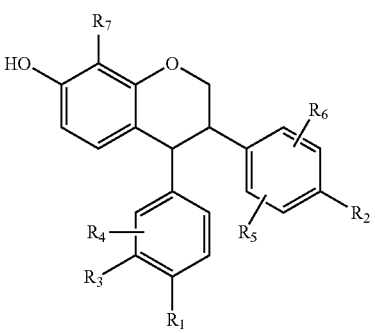

Formula (II-a)

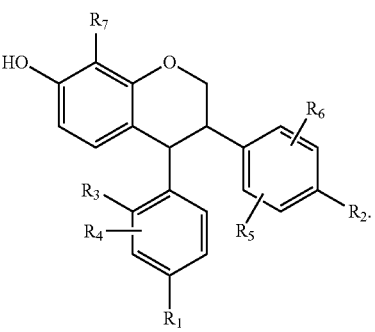

Formula (II-b)

In some embodiments, $R_1$ is hydroxy. In other embodiments, $R_1$ is $C_1$-$C_6$alkoxy. In further or additional embodiments, $R_1$ is $C_1$-$C_3$alkoxy. In other embodiments, $R_1$ is $C_1$-$C_2$alkoxy. In specific embodiments, $R_1$ is methoxy. In specific embodiments, $R_1$ is ethoxy. In specific embodiments, $R_1$ is propoxy. In specific embodiments, $R_1$ is iso-propoxy. In specific embodiments, $R_1$ is butoxy. In specific embodiments, $R_1$ is iso-butoxy. In specific embodiments, $R_1$ is sec-butoxy. In specific embodiments, $R_1$ is tert-butoxy. In specific embodiments, $R_1$ is pentyloxy. In specific embodiments, $R_1$ is hexyloxy. In further or alternative embodiments, $R_1$ is fluoro. In other embodiments, $R_1$ is chloro. In other embodiments, $R_1$ is iodo. In other embodiments, $R_1$ is bromo. In other embodiments, $R_1$ is haloalkyl. In other embodiments, $R_1$ is halo$C_{1-6}$alkyl. In other embodiments, $R_1$ is halo$C_{1-3}$alkyl. In other embodiments, $R_1$ is halo$C_{1-2}$alkyl. In specific embodiments, $R_1$ is monofluoromethyl. In specific embodiments, $R_1$ is difluoromethyl. In specific embodiments, $R_1$ is trifluoromethyl.

In further or additional embodiments, $R_2$ is hydroxy. In some embodiments, $R_2$ is $C_1$-$C_6$alkoxy. In further or additional embodiments, $R_2$ is $C_1$-$C_3$alkoxy. In further or additional embodiments, $R_2$ is $C_1$-$C_2$alkoxy. In specific embodiments, $R_2$ is methoxy. In specific embodiments, $R_2$ is ethoxy. In specific embodiments, $R_2$ is propoxy. In specific embodiments, $R_2$ is iso-propoxy. In specific embodiments, $R_2$ is butoxy. In specific embodiments, $R_2$ is iso-butoxy. In specific embodiments, $R_2$ is sec-butoxy. In specific embodiments, $R_2$ is tert-butoxy. In specific embodiments, $R_2$ is pentyloxy. In specific embodiments, $R_2$ is hexyloxy.

In some embodiments, compounds of the general formula (II) have the substituents $R_1$, $R_3$ and $R_4$ distributed as shown below:

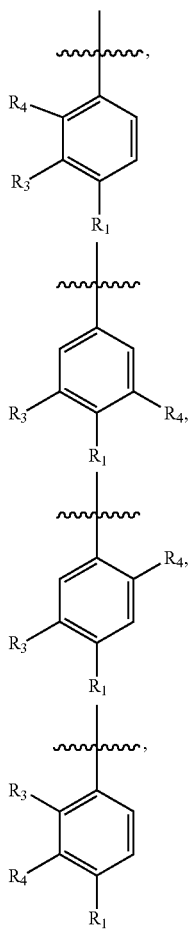

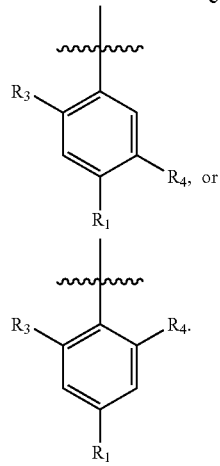

In further or additional embodiments, $R_3$ is $C_1$-$C_6$alkyl. In other embodiments, $R_3$ is $C_1$-$C_3$alkyl. In other embodiments, $R_3$ is $C_1$-$C_2$alkyl. In specific embodiments, $R_3$ is methyl. In specific embodiments, $R_3$ is ethyl. In specific embodiments, $R_3$ is propyl. In specific embodiments, $R_3$ is iso-propyl. In specific embodiments, $R_3$ is butyl. In specific embodiments, $R_3$ is iso-butyl. In specific embodiments, $R_3$ is sec-butyl. In specific embodiments, $R_3$ is tert-butyl. In specific embodiments, $R_3$ is pentyl. In specific embodiments, $R_3$ is hexyl. In further or alternative embodiments, $R_3$ is fluoro. In other embodiments, $R_3$ is chloro. In other embodiments, $R_3$ is iodo. In other embodiments, $R_3$ is bromo. In other embodiments, $R_3$ is haloalkyl. In other embodiments, $R_3$ is halo$C_{1-6}$alkyl. In other embodiments, $R_3$ is halo$C_{1-3}$alkyl. In other embodiments, $R_3$ is halo$C_{1-2}$alkyl. In specific embodiments, $R_3$ is monofluoromethyl. In specific embodiments, $R_3$ is difluoromethyl. In specific embodiments, $R_3$ is trifluoromethyl.

In further or additional embodiments, $R_4$ is hydrogen. In further or alternative embodiments, $R_4$ is halo. In specific embodiments, $R_4$ is fluoro. In other embodiments, $R_4$ is haloalkyl. In other embodiments, $R_4$ is halo$C_{1-6}$alkyl. In other embodiments, $R_4$ is halo$C_{1-3}$alkyl. In other embodiments, $R_4$ is halo$C_{1-2}$alkyl. In specific embodiments, $R_4$ is monofluoromethyl. In specific embodiments, $R_4$ is difluoromethyl. In specific embodiments, $R_4$ is trifluoromethyl. In further or alternative embodiments, $R_4$ is $C_1$-$C_6$alkyl. In other embodiments, $R_4$ is $C_1$-$C_3$alkyl. In other embodiments, $R_4$ is $C_1$-$C_2$alkyl. In specific embodiments, $R_4$ is methyl. In specific embodiments, $R_4$ is ethyl. In specific embodiments, $R_4$ is propyl. In specific embodiments, $R_4$ is iso-propyl.

Some embodiments provided herein describe a compound of formula II wherein $R_5$ and $R_6$ are hydrogen. In specific embodiments, $R_5$ is hydrogen. In other specific embodiments, $R_6$ is hydrogen.

In other embodiments, $R_5$ is alkyl. In other embodiments, $R_5$ is $C_1$-$C_6$alkyl. In other embodiments, $R_5$ is $C_1$-$C_3$alkyl. In other embodiments, $R_5$ is $C_1$-$C_2$alkyl. In specific embodiments, $R_5$ is methyl. In specific embodiments, $R_5$ is ethyl. In specific embodiments, $R_5$ is propyl. In specific embodiments, $R_5$ is iso-propyl. In other embodiments, $R_5$ is halo. In other embodiments, $R_5$ is fluoro. In other embodiments, $R_5$ is bromo. In other embodiments, $R_5$ is chloro. In other embodiments, $R_5$ is iodo. In other embodiments, $R_5$ is haloalkyl. In other embodiments, $R_5$ is halo$C_{1-6}$alkyl. In other embodiments, $R_5$ is halo$C_{1-3}$alkyl. In other embodiments, $R_5$ is halo$C_{1-2}$alkyl. In specific embodiments, $R_5$ is monofluoromethyl. In specific embodiments, $R_5$ is difluoromethyl. In specific embodiments, $R_5$ is trifluoromethyl.

In still further or alternative embodiments, $R_6$ is alkyl, haloalkyl or halo. In other embodiments, $R_6$ is alkyl. In other embodiments, $R_6$ is $C_1$-$C_6$alkyl. In other embodiments, $R_6$ is $C_1$-$C_3$alkyl. In other embodiments, $R_6$ is $C_1$-$C_2$alkyl. In specific embodiments, $R_6$ is methyl. In specific embodiments, $R_6$ is ethyl. In specific embodiments, $R_6$ is propyl. In specific embodiments, $R_6$ is iso-propyl. In other embodiments, $R_6$ is halo. In other embodiments, $R_6$ is fluoro. In other embodiments, $R_6$ is bromo. In other embodiments, $R_6$ is chloro. In other embodiments, $R_6$ is iodo. In other embodiments, $R_6$ is haloalkyl. In other embodiments, $R_6$ is halo$C_{1-6}$alkyl. In other embodiments, $R_6$ is halo$C_{1-3}$alkyl. In other embodiments, $R_6$ is halo$C_{1-2}$alkyl. In specific embodiments, $R_6$ is monofluoromethyl. In specific embodiments, $R_6$ is difluoromethyl. In specific embodiments, $R_6$ is trifluoromethyl.

In some embodiments, $R_7$ is $C_1$-$C_6$alkyl. In other embodiments, $R_7$ is $C_1$-$C_3$alkyl. In other embodiments, $R_7$ is $C_1$-$C_2$alkyl. In specific embodiments, $R_7$ is methyl. In specific embodiments, $R_7$ is ethyl. In specific embodiments, $R_7$ is propyl. In specific embodiments, $R_7$ is isopropyl. In alternative embodiments, $R_7$ is hydrogen.

Provided herein, in some embodiments, is a pharmaceutical composition comprising a compound (i.e., isoflavonoid derivative) of formula III:

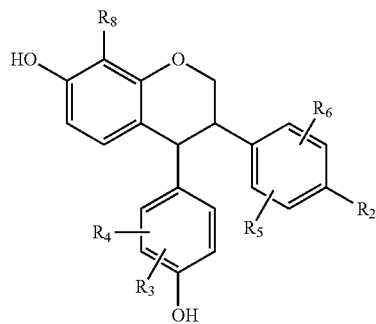

wherein
$R_2$ is hydroxy or alkoxy;
$R_3$, $R_4$, $R_5$, and $R_6$ are independently hydrogen, hydroxy, alkoxy, halo, haloalkyl, or alkyl; and
$R_7$ is alkyl;
or a pharmaceutically acceptable salt thereof.

Some embodiments provided herein describe a compound of Formula III that has a structure of Formula (III-a) or (III-b):

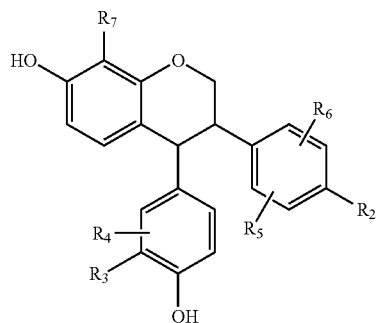

Formula (III-a)

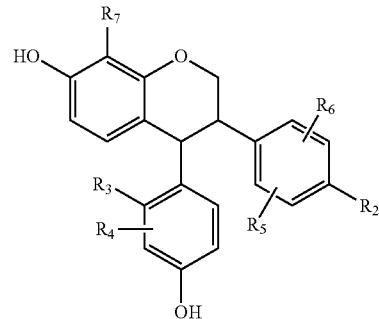

Formula (III-b)

In some embodiments, $R_2$ is hydroxy. In other embodiments, $R_2$ is $C_1$-$C_6$alkoxy. In further or additional embodiments, $R_2$ is $C_1$-$C_3$alkoxy. In specific embodiments, $R_2$ is methoxy, ethoxy, propoxy, iso-propoxy, butoxy, iso-butoxy, sec-butoxy, tert-butoxy, pentyloxy or hexyloxy. In specific embodiments, $R_2$ is methoxy.

In further or additional embodiments, $R_3$ is $C_1$-$C_6$alkyl. In other embodiments, $R_3$ is $C_1$-$C_3$alkyl. In other embodiments, $R_3$ is $C_1$-$C_2$alkyl. In other embodiments, $R_3$ is methyl. In other embodiments, $R_3$ is ethyl. In other embodiments, $R_3$ is propyl. In other embodiments, $R_3$ is iso-propyl. In other embodiments, $R_3$ is butyl. In other embodiments, $R_3$ is iso-butyl. In other embodiments, $R_3$ is sec-butyl. In other embodiments, $R_3$ is tert-butyl. In other embodiments, $R_3$ is pentyl. In other embodiments, $R_3$ is hexyl. In alternative embodiments, $R_3$ is hydrogen. In other embodiments, $R_3$ is halo. In other embodiments, $R_3$ is fluoro. In other embodiments, $R_3$ is chloro. In other embodiments, $R_3$ is bromo. In other embodiments, $R_3$ is haloalkyl. In other embodiments, $R_3$ is halo$C_{1-6}$alkyl. In other embodiments, $R_3$ is halo$C_{1-3}$alkyl. In other embodiments, $R_3$ is halo$C_{1-2}$alkyl. In specific embodiments, $R_3$ is monofluoromethyl. In specific embodiments, $R_3$ is difluoromethyl. In specific embodiments, $R_3$ is trifluoromethyl.

In further or additional embodiments, $R_4$ is hydrogen. In further or alternative embodiments, $R_4$ is halo. In specific embodiments, $R_4$ is fluoro. In specific embodiments, $R_4$ is chloro. In specific embodiments, $R_4$ is bromo. In other embodiments, $R_4$ is haloalkyl. In other embodiments, $R_4$ is halo$C_{1-6}$alkyl. In other embodiments, $R_4$ is halo$C_{1-3}$alkyl. In other embodiments, $R_4$ is halo$C_{1-2}$alkyl. In specific embodiments, $R_4$ is monofluoromethyl. In specific embodiments, $R_4$ is difluoromethyl. In specific embodiments, $R_4$ is trifluoromethyl. In other embodiments, $R_4$ is $C_1$-$C_6$alkyl. In other embodiments, $R_4$ is $C_1$-$C_3$alkyl. In other embodiments, $R_4$ is $C_1$-$C_2$alkyl. In other embodiments, $R_4$ is methyl. In other embodiments, $R_4$ is ethyl. In other embodiments, $R_4$ is propyl. In other embodiments, $R_4$ is iso-propyl.

In some embodiments, $R_7$ is $C_1$-$C_6$alkyl. In other embodiments, $R_7$ is $C_1$-$C_3$alkyl. In other embodiments, $R_7$ is $C_1$-$C_2$alkyl. In specific embodiments, $R_7$ is methyl. In other embodiments, $R_7$ is ethyl. In other embodiments, $R_7$ is propyl. In other embodiments, $R_7$ is iso-propyl. In other embodiments, $R_7$ is butyl. In other embodiments, $R_7$ is iso-butyl. In other embodiments, $R_7$ is sec-butyl. In other embodiments, $R_7$ is tert-butyl. In other embodiments, $R_7$ is pentyl. In other embodiments, $R_7$ is hexyl.

In some embodiments, compounds of the general Formula III have the substituents $R_3$ and $R_4$ distributed as shown below:

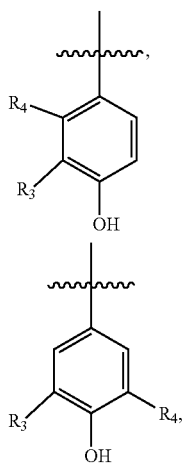
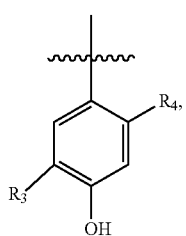
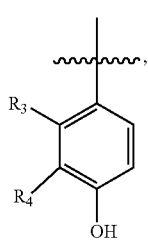
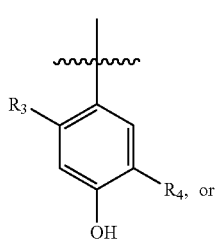
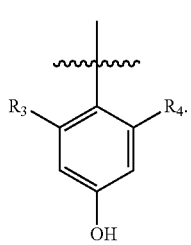
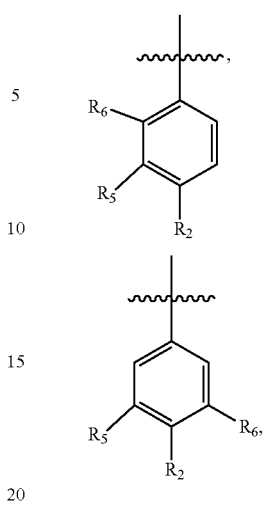
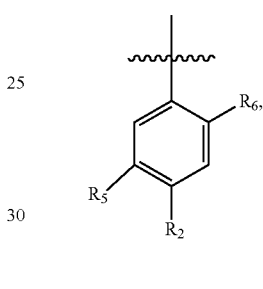
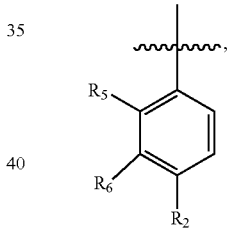
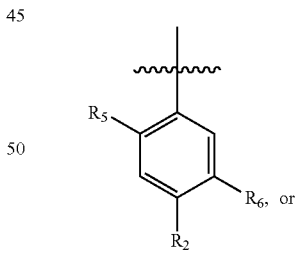
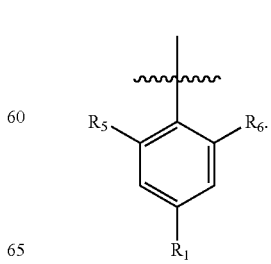
In some embodiments, compounds of the general Formula I, II, or III have the substituents $R_2$, $R_5$, and $R_6$ distributed as shown below:

Specific compounds of Formula I, II, or III are shown below:
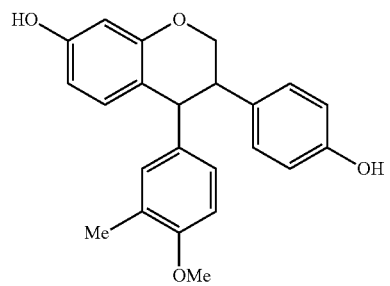
(1)
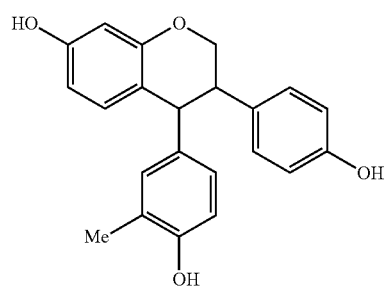
(2)
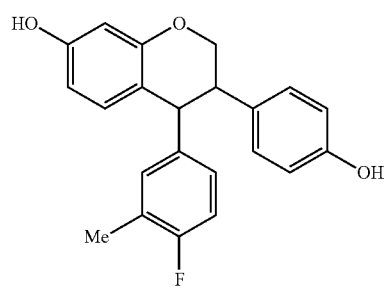
(3)
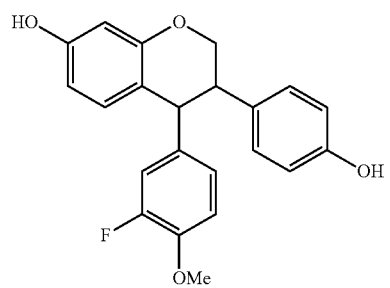
(4)
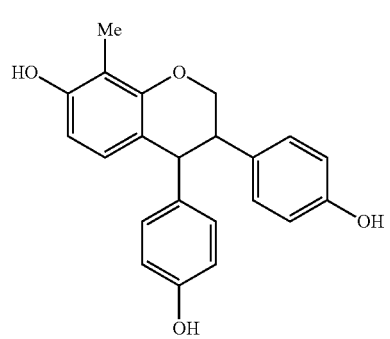
(5)
-continued
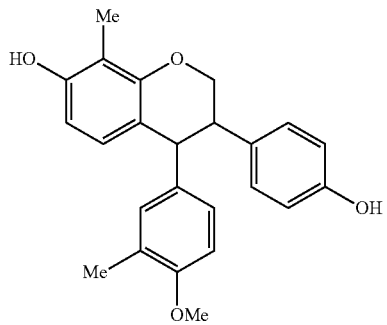
(6)
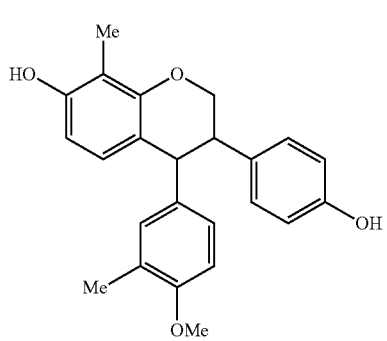
(7)
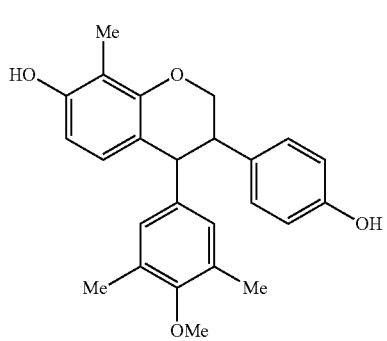
(8)
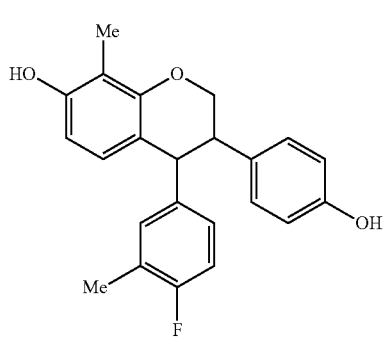
(9)
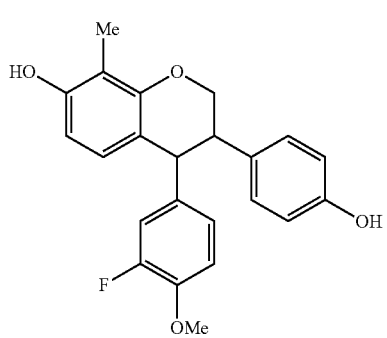
(10)
or salts or a derivative thereof.

In specific embodiments, a compound of Formula I, II, or III include:

3-(4-hydroxyphenyl)-4-(4-methoxy-3-methylphenyl)chroman-7-ol (compound 1);
3-(4-hydroxyphenyl)-4-(4-hydroxy-3-methylphenyl)chroman-7-ol (compound 2);
3-(4-hydroxyphenyl)-4-(4-fluoro-3-methylphenyl)chroman-7-ol (compound 3);
3-(4-hydroxyphenyl)-4-(4-methoxy-3-fluorophenyl)chroman-7-ol (compound 4);
3-(4-hydroxyphenyl)-4-(4-hydroxyphenyl)-8-methylchroman-7-ol (compound 5);
3-(4-hydroxyphenyl)-4-(4-hydroxy-3-methylphenyl)-8-methylchroman-7-ol (compound 6);
3-(4-hydroxyphenyl)-4-(4-methoxy-3-methylphenyl)-8-methylchroman-7-ol (compound 7);
3-(4-hydroxyphenyl)-4-(4-methoxy-3,5-dimethylphenyl)-8-methylchroman-7-ol (compound 8);
3-(4-hydroxyphenyl)-4-(4-fluoro-3-methylphenyl)-8-methylchroman-7-ol (compound 9); and
3-(4-hydroxyphenyl)-4-(4-methoxy-3-fluorophenyl)-8-methylchroman-7-ol (compound 10).

It will be clear to persons skilled in the art that in the compounds according to certain embodiments of the invention, the aryl substituents on the heterocyclic ring can be cis or trans relative to each other. Preferably in the compounds of Formula I, II, or III according to certain embodiments of the invention, these substituents will be cis.

The compounds of Formula I, II, or III according to some embodiments of this invention include two chiral centers. The present invention includes all the enantiomers and diastereomers as well as mixtures thereof in any proportions. The invention also extends to isolated enantiomers or pairs of enantiomers. Some of the compounds herein (including, but not limited to isoflavonoid derivatives and reagents for producing the aforementioned compounds) have asymmetric carbon atoms and can therefore exist as enantiomers or diastereomers. Diastereomeric mixtures can be separated into their individual diastereomers on the basis of their physical chemical differences by methods such as chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The compounds of Formula I, II, or III according to some embodiments are racemic mixture. In other embodiments, any compound described herein is in the optically pure form (e.g., optically active (+) and (−), (R)- and (S)-, d- and l-, or (D)- and (L)-isomers). In certain preferred embodiments, a compound of Formula I, II, or III is the d-isomer. Accordingly, provided herein, in some embodiments, is the optically active d-isomer having a structure of Formula I, II, or III in enantiomeric excess. In some embodiments, the d-isomer of a compound of Formulas I, II, or III is provided in at least 50%, 55%, 60%, 65%, 70%, 75%, 80%, 85%, 88%, 90%, 91%, 92%, 93%, 94%, 95%, 96%, 97%, 98%, 99%, 95%, or 99.9% enantiomeric excess. In other embodiments, the d-isomer of a compound of Formulas I, II, or III is provided in greater than 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess. In specific embodiments, of a compound of Formulas I, II, or III has greater than 95% enantiomeric excess.

Specific optically active compounds (i.e., enantiomers) of Formula I, II, or III are shown below:

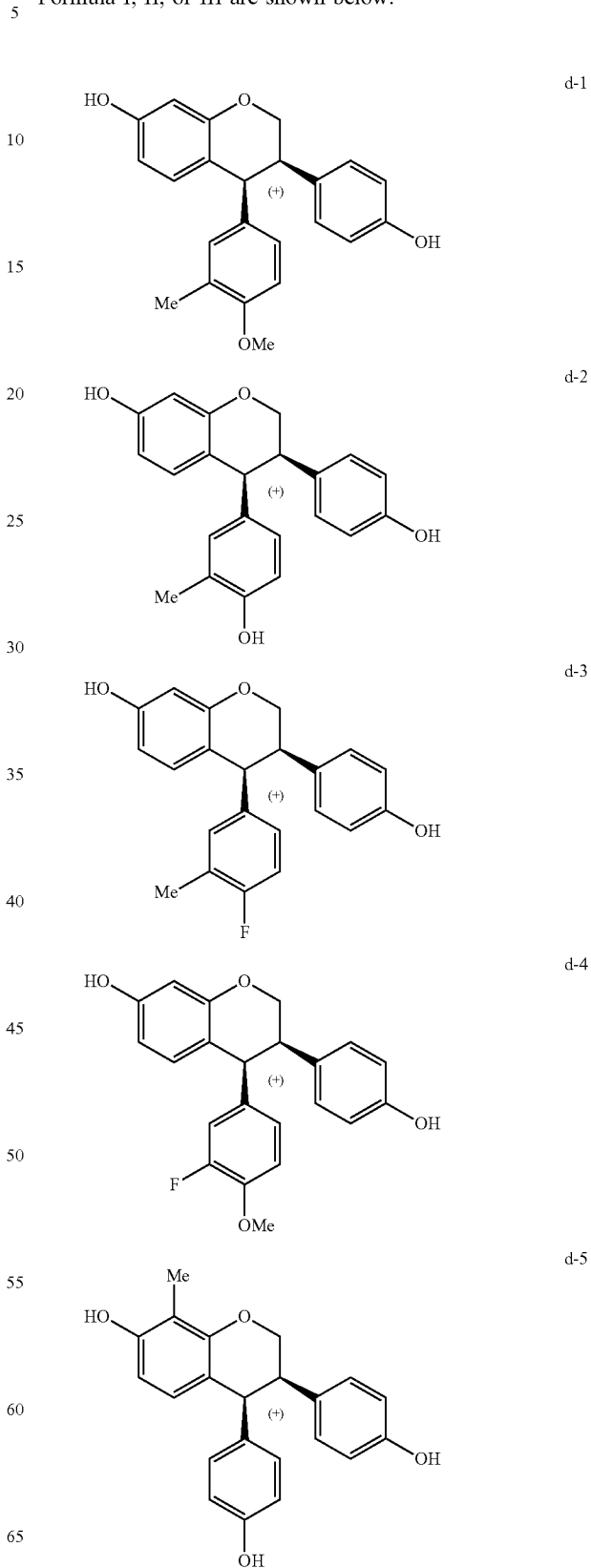

-continued
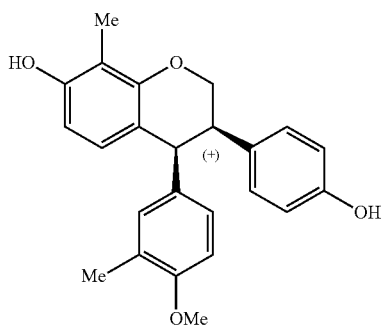
d-6
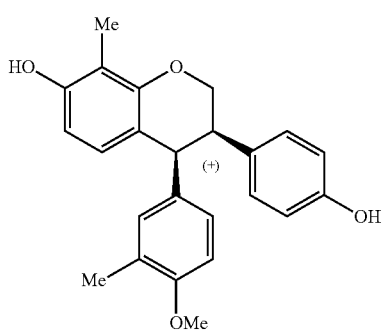
d-7
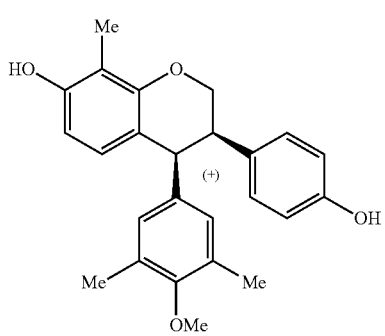
d-8
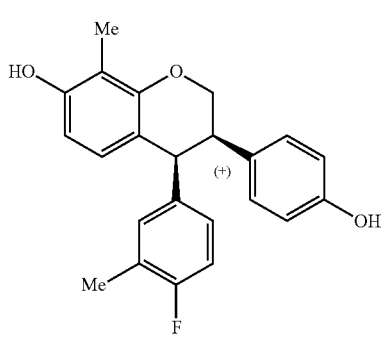
d-9
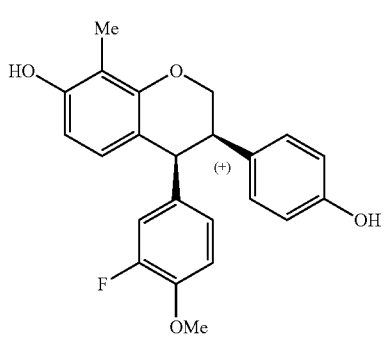
d-10
-continued
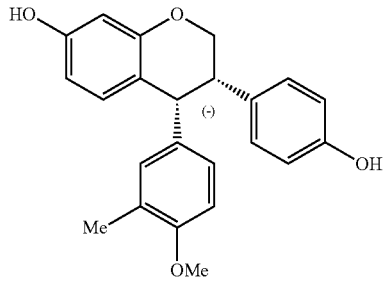
l-1
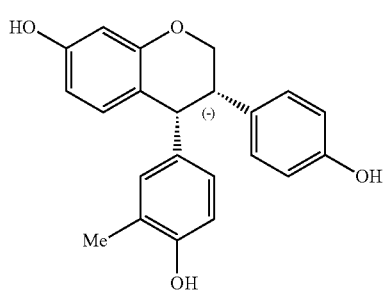
l-2
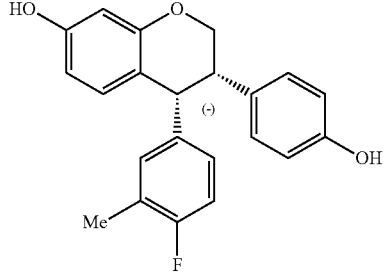
l-3
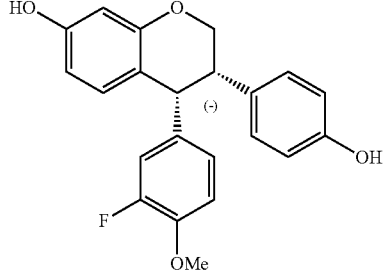
l-4
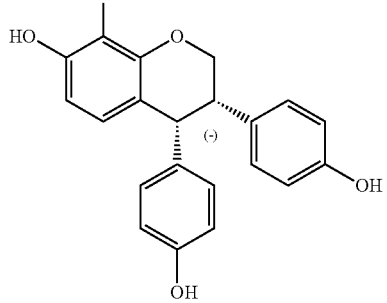
l-5

-continued

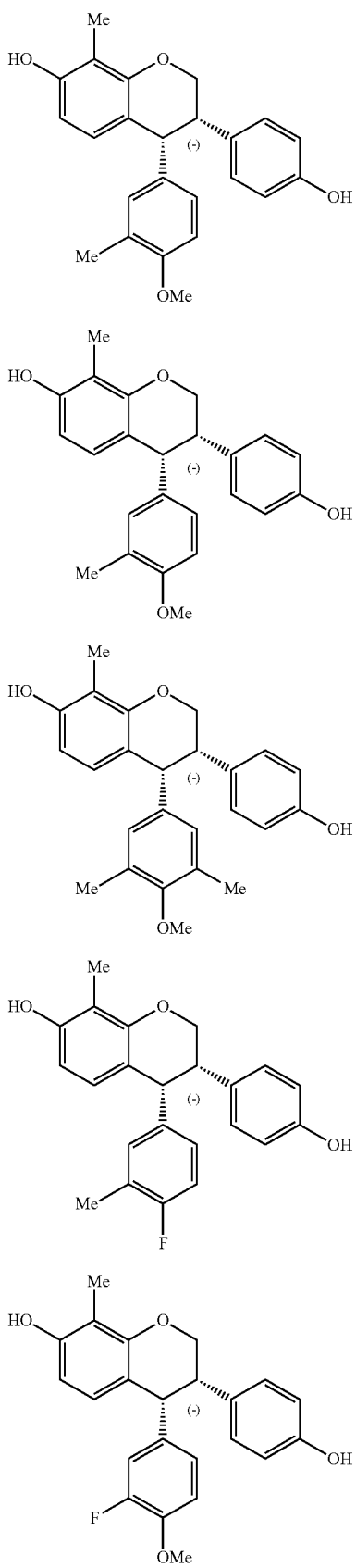

In specific embodiments, a compound of Formula I, II, or III include:

I-6
d-cis-3-(4-hydroxyphenyl)-4-(4-methoxy-3-methylphenyl) chroman-7-ol (d-1);
d-cis-3-(4-hydroxyphenyl)-4-(4-hydroxy-3-methylphenyl) chroman-7-ol (d-2);
d-cis-3-(4-hydroxyphenyl)-4-(4-fluoro-3-methylphenyl) chroman-7-ol (d-3);
d-cis-3-(4-hydroxyphenyl)-4-(4-methoxy-3-fluorophenyl) chroman-7-ol (d-4);
d-cis-3-(4-hydroxyphenyl)-4-(4-hydroxyphenyl)-8-methyl-chroman-7-ol (d-5);

I-7
d-cis-3-(4-hydroxyphenyl)-4-(4-hydroxy-3-methylphenyl)-8-methylchroman-7-ol (d-6);
d-cis-3-(4-hydroxyphenyl)-4-(4-methoxy-3-methylphenyl)-8-methylchroman-7-ol (d-7),
d-cis-3-(4-hydroxyphenyl)-4-(4-methoxy-3,5-dimethylphenyl)-8-methylchroman-7-ol (d-8);
d-cis-3-(4-hydroxyphenyl)-4-(4-fluoro-3-methylphenyl)-8-methylchroman-7-ol (d-9), and
d-cis-3-(4-hydroxyphenyl)-4-(4-methoxy-3-fluorophenyl)-8-methylchroman-7-ol (d-10).

I-8
In other specific embodiments, a compound of Formula I, II, or III include:
l-cis-3-(4-hydroxyphenyl)-4-(4-methoxy-3-methylphenyl) chroman-7-ol (l-1);
l-cis-3-(4-hydroxyphenyl)-4-(4-hydroxy-3-methylphenyl) chroman-7-ol (l-2);
l-cis-3-(4-hydroxyphenyl)-4-(4-fluoro-3-methylphenyl) chroman-7-ol (l-3);
l-cis-3-(4-hydroxyphenyl)-4-(4-methoxy-3-fluorophenyl) chroman-7-ol (l-4);
l-cis-3-(4-hydroxyphenyl)-4-(4-hydroxyphenyl)-8-methyl-chroman-7-ol (l-5);

I-9
l-cis-3-(4-hydroxyphenyl)-4-(4-hydroxy-3-methylphenyl)-8-methylchroman-7-ol (l-6);
l-cis-3-(4-hydroxyphenyl)-4-(4-methoxy-3-methylphenyl)-8-methylchroman-7-ol (l-7);
l-cis-3-(4-hydroxyphenyl)-4-(4-methoxy-3,5-dimethylphenyl)-8-methylchroman-7-ol (l-8);
l-cis-3-(4-hydroxyphenyl)-4-(4-fluoro-3-methylphenyl)-8-methylchroman-7-ol (l-9); and
l-cis-3-(4-hydroxyphenyl)-4-(4-methoxy-3-fluorophenyl)-8-methylchroman-7-ol (l-10).

I-10
Some embodiments provided herein describe a compound of Formula IV wherein $R_8$ is hydrogen or alkyl. In some embodiments, $R_8$ is hydrogen. In other embodiments, $R_8$ is $C_{1-6}$alkyl. In other embodiments, $R_8$ is $C_{1-3}$alkyl. In other embodiments, $R_8$ is $C_{1-2}$alkyl. In specific embodiments, $R_8$ is methyl. In specific embodiments, $R_8$ is ethyl. In specific embodiments, $R_8$ is propyl. In specific embodiments, $R_8$ is iso-propyl. In specific embodiments, $R_8$ is butyl. In specific embodiments, $R_8$ is iso-butyl. In specific embodiments, $R_8$ is sec-butyl. In specific embodiments, $R_8$ is tert-butyl. In specific embodiments, $R_8$ is pentyl. In specific embodiments, $R_8$ is hexyl.

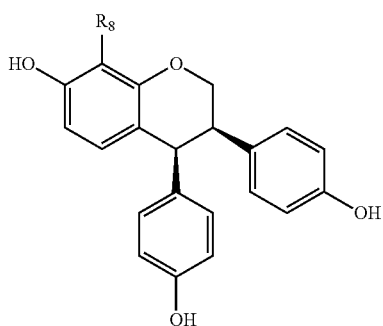

Formula (IV)

Specific optically active compounds (i.e., enantiomers) of Formula IV include:

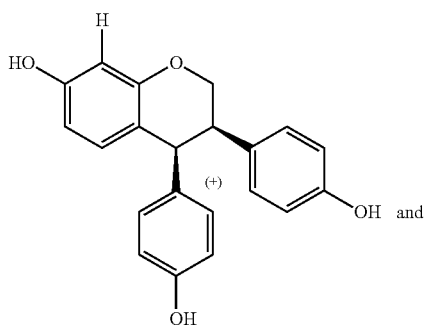

(31)

and

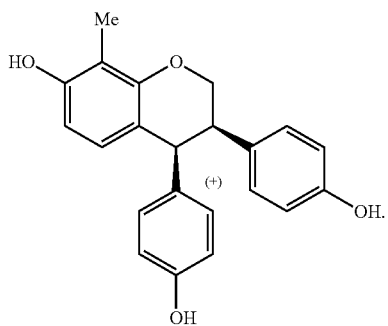

d-5

In specific embodiments, a compound of Formula IV includes d-cis-3-(4-hydroxyphenyl)-4-(4-hydroxyphenyl)chroman-7-ol. In other embodiments, a compound of Formula IV includes d-cis-3-(4-hydroxyphenyl)-4-(4-hydroxyphenyl)-8-methylchroman-7-ol.

In certain preferred embodiments, a compound of Formula IV is the d-isomer. Accordingly, provided herein, in some embodiments, is the optically active d-isomer having a structure of Formula IV in enantiomeric excess. In some embodiments, the d-isomer of a compound of Formula IV is provided in at least 50%, 55%, 60%, 65%, 70%, 75%, 80%, 85%, 88%, 90%, 91%, 92%, 93%, 94%, 95%, 96%, 97%, 98%, 99%, 95.5%, or 99.9% enantiomeric excess. In other embodiments, the d-isomer of a compound of Formula IV is provided in greater than 50%, 55%, 60%, 65%, 70%, 75%, 80%, 85%, 88%, 90%, 91%, 92%, 93%, 94%, 95%, 96%, 97%, 98%, 99%, 99.5%, or 99.9% enantiomeric excess. In specific embodiments, a compound of Formula IV has greater than 95% enantiomeric excess. In specific embodiments, a compound of Formula IV has greater than 98% enantiomeric excess. In specific embodiments, a compound of Formula IV has greater than 99% enantiomeric excess. In specific embodiments, a compound of Formula IV has greater than 99.9% enantiomeric excess.

In additional or further embodiments, the compounds described herein are used in the form of pro-drugs. In additional or further embodiments, the compounds described herein are metabolized upon administration to an organism in need to produce a metabolite that is then used to produce a desired effect, including a desired therapeutic effect.

Any compound described herein may be synthesized according to the exemplary synthesis shown in Schemes 1 and 2. For example, compounds 6 and 7 are synthesized from 4'-bis-tert-butyldimethylsilyloxy-8-methyldihydrodaidzein. 4'-bis-tert-butyldimethylsilyloxy-8-methyldihydrodaidzein is treated with 4-methoxy-3-methylphenylmagnesium bromide in anhydrous THF. The reaction mixture is treated with wet ether (50:50 $H_2O/Et_2O$). The resultant mixture is extracted with $Et_2O$. The organic layer is washed with water, brine, dried over anhydrous magnesium sulfate and concentrated in vacuo. The resultant residue is treated with pTsOH and ethanol. The reaction mixture is heated to reflux for 3 hours. The reaction mixture is concentrated in vacuo then poured into water (0° C.). The mixture is extracted with EtOAc, then the organic layer is washed with water (3×), brine, dried ($MgSO_4$), filtered and concentrated in vacuo to provide the 3-alkene intermediate. The intermediate is treated with Pd catalyst and ethanol. The reaction mixture is hydrogenated at low pressure for 3 h. The reaction is filtered through Celite and the filtrate is concentrated to a volume of 15 mL. The resultant solution is added to water. The mixture is extracted with $Et_2O$ (3×), the organic layers are combined and washed with water, brine, dried ($MgSO_4$), filtered and concentrated in vacuo. The resultant residue is purified by recrystallization to provide compound 7.

Scheme 1

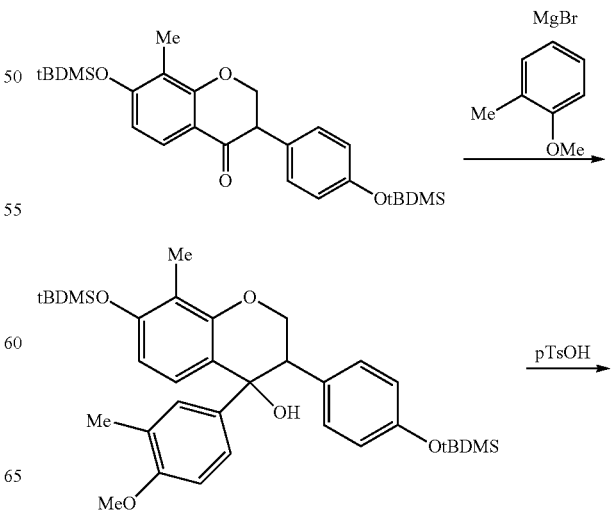

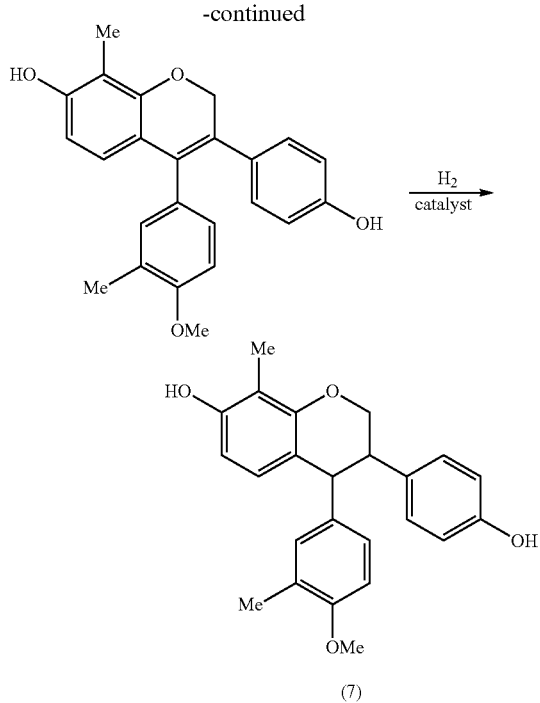

(7)

Compound 7 is transferred to a flask purged with nitrogen. Hydrogen bromide in acetic acid (33 wt %) is added drop-wise to the reaction mixture. The mixture is heated to reflux at 130° C. for 7 h. The reaction mixture is placed in an ice bath and the pH is adjusted 6. The reaction mixture is extracted with EtOAc and the organic layer is washed with water, brine, dried ($MgSO_4$), filtered and concentrated in vacuo. The resultant residue is purified by column chromatography to yield compound 6.

Scheme 2

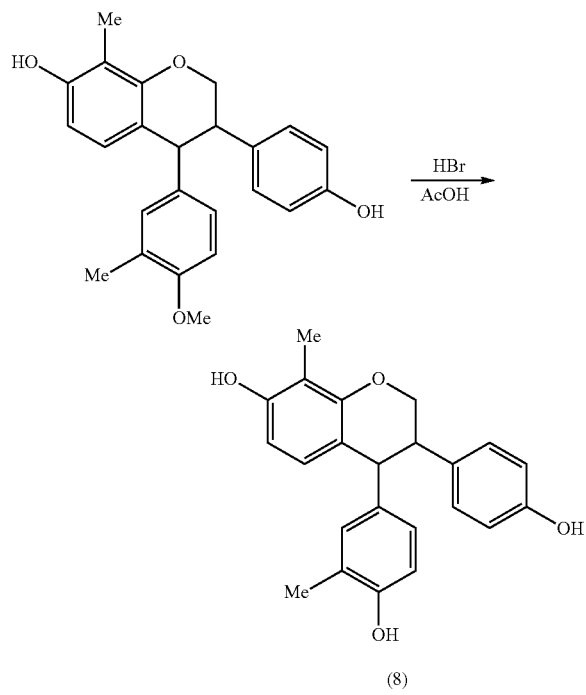

(8)

Methods

Some embodiments provided herein describe a method of inducing apoptosis in a cancer cell. In specific embodiments, the method comprises contacting the cancer cell with a composition comprising an isoflavonoid derivative of Formula I, II, III, or IV. Also described herein, in other embodiments, is a method of treating cancer in an individual in need of cancer therapy. In certain embodiments, the method comprises administering to the individual the composition comprising a compound (i.e., isoflavonoid derivative) of Formula I, II, III, or IV. In certain embodiments, the cancer or cancer cell is present in an individual. In specific embodiments, the individual is in need of cancer therapy.

In other embodiments, provided herein is a method of increasing, inducing, or restoring sensitivity of a cancer cell to a chemotherapeutic agent, anti-cancer agent or radiation therapy. In certain embodiments, the method comprises contacting said cell with a composition comprising a compound (i.e., isoflavonoid derivative) of Formula I, II, III, or IV. In other embodiments, provided herein is a method of increasing, inducing, or restoring sensitivity to a cancer therapy in an individual. In certain embodiments, the method comprises administering to the individual a composition comprising a compound (i.e., isoflavonoid derivative) of Formula I, II, III, or IV.

In some embodiments, the cancer or cancer cell has lost sensitivity to a chemotherapeutic agent, anti-cancer agent or radiation therapy. In other embodiments, the combination of a composition comprising a compound of Formula I, II, III, or IV and a chemotherapeutic agent, anti-cancer agent or radiation therapy has an enhanced effect. In some embodiments, the compounds described herein chemosensitize cancer cells, wherein compounds lower the amount of anti-cancer agent that is required to kill the cancer cell. In other embodiments, the compounds described herein chemosensitize cancer cells, wherein the compounds convert cancer cells from a state of chemo-resistant to chemo-sensitive. In further or additional embodiments, the compounds described herein radiosensitize cancer cells, wherein compounds lower the amount of gamma-irradiation that is required to kill the cancer cell. In other embodiments, the compounds described herein radiosensitize cancer cells, wherein the compounds convert cancer cells from a state of radio-resistant to radio-sensitive.

Provided herein in some embodiments, is a method to treat cancer in an individual, comprising administering to the individual a composition comprising a compound (i.e., isoflavonoid derivative) of Formula I, II, III, or IV, wherein the side-effects associated with chemotherapy, radiotherapy, or cancer therapy is reduced or minimized. In some instances, the compounds described herein provide chemo-protective and/or radio-protective properties to non-cancerous cells. In other embodiments, the use of the d-isomer of the compounds described herein lowers the amount of the compound that is required to kill the cancer cell or treat the cancer. In further or additional embodiments, the lower amount of compound reduces or minimizes any undesired side-effects associated with chemotherapy. Non-limiting examples of side-effects associated with chemotherapy, radiotherapy or cancer therapy include fatigue, anemia, appetite changes, bleeding problems, diarrhea, constipation, hair loss, nausea, vomiting, pain, peripheral neuropathy, swelling, skin and nail changes, urinary and bladder changes, and trouble swallowing.

Any of the method described herein, in some embodiments, further comprise administering cancer therapy to the individual or patient. In certain embodiments, the cancer therapy is, by way of non-limiting example, at least one anti-cancer agent (e.g., chemotherapeutic agent), radiation therapy, or surgery. In some embodiments, a combination of (1) administration of an effective amount of a compound described herein and (2) 1 to 3 therapies selected from the group consisting of (i) administration of an effective amount of an additional anticancer agents, (ii) administration of an effective amount of hormonal therapeutic agents and (iii) non-drug therapy prevents and/or treats cancer more effectively.

An anti-cancer agent includes but is not limited to a chemotherapeutic agent, immunotherapeutic agent, a pharmaceutical agent that inhibits the action of cell growth factor and a receptor thereof and the like. Among the chemotherapeutic agents that are optionally employed, by way of non-limiting example, are cisplatin, carboplatin, paclitaxel, gemcitabine or doxorubicin. Further, non-limiting examples of chemotherapeutic agents include alkylating agents, antimetabolites, anticancer antibiotics, plant-derived anticancer agents, and the like.

Alkylating agents include but are not limited to nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and the like.

Antimetabolites include but are not limited to mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Anticancer antibiotics include but are not limited to actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epiubicin hydrochloride, neocarzinostatin, mithramycin, sarcomycin, carzinophilin, mitotane, zorubicin hydrochloride, mitoxantrone hydrochloride, idarubicin hydrochloride, and the like.

Plant-derived anticancer agents include but are not limited to etoposide, etoposide phosphate, vinblastine sulfate, vincristine sulfate, vindesine sulfate, teniposide, paclitaxel, docetaxel, vinorelbine, and the like.

Immunotherapeutic agents include but are not limited to picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebaclerium parvum*, levamisole, polysaccharide K, procodazole, and the like.

Non-limiting examples of a cell growth factor in pharmaceutical agents that inhibit the action of cell growth factors or cell growth factor receptors include any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin, and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

Cell growth factor receptors include but are not limited to any receptors capable of binding to the aforementioned cell growth factors, including EGF receptor, heregulin receptor (HER2), insulin receptor, IGF receptor, FGF receptor-1 or FGF receptor-2, and the like.

Pharmaceutical agent that inhibits the action of cell growth factor include but are not limited to HER2 antibody (e.g., trastuzumab), imatinib mesylate, ZD1839 or EGFR antibody (e.g., cetuximab), antibody to VEGF (e.g., bevacizumab), VEGFR antibody, VEGFR inhibitor, and EGFR inhibitor (e.g., erlotinib).

In addition to the aforementioned drugs, other anti-cancer agents include but are not limited to L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitors (e.g., thalidomide, SU11248, and the like), α-blockers (e.g., tamsulosin hydrochloride, naftopidil, urapidil, alfuzosin, terazosin, prazosin, silodosin, and the like) serine/threonine kinase inhibitor, endothelin receptor antagonist (e.g., atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like.

Non-limiting examples of hormonal therapeutic agents include fosfestrol, diethylstylbestrol, chlortrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down-regulator (e.g., fulvestrant and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocoticohormone drugs (e.g., dexamethasone, prednisolone, betamethasone, triamcinolone, and the like), androgen synthesis inhibitors (e.g., abiraterone, and the like), and retinoid and drugs that retard retinoid metabolism (e.g., liarozole, and the like), etc. and LH-RH agonists (e.g., goserelin acetate, buserelin, leuprorelin).

The non-drug therapy is exemplified by surgery, radiotherapy, gene therapy, thermotherapy, cryotherapy, laser cauterization, and the like, and any combinations thereof.

When a compound (i.e., isoflavonoid derivative) of Formula I, II, III, or IV and a concomitant drug are used in combination, the administration time of the isoflavonoid derivative and the concomitant drug is not restricted. In some embodiments, the isoflavonoid derivative and the concomitant drug are administered to an individual simultaneously. In other embodiments, the isoflavonoid derivative and the concomitant drug are administered at staggered times.

In some embodiments, the cancer is selected from the group consisting of bladder cancer, breast cancer, metastatic breast cancer, metastatic HER2-negative breast cancer, colon cancer, rectal cancer, metastatic colorectal cancer, endometrial cancer, cervical cancer, uterine cancer, ovarian cancer, kidney cancer, liver cancer, leukemia, lung cancer (both small cell and non-small cell), squamous non-small cell lung cancer, non-squamous non-small cell lung cancer, melanoma, non-Hodgkin lymphoma, pancreatic cancer, testicular cancer, prostate cancer, thyroid cancer, sarcoma (including osteosarcoma), esophageal cancer, gastric cancer, head and neck cancer, lung cancer melanoma, myeloma, neuroblastoma, glioblastoma, and cancers of the brain. In some embodiments, the cancer is selected from, by way of non-limiting example, human breast, prostate, ovarian, pancreatic, or cervical cancer. In certain specific embodiments, the cancer is human breast cancer or ovarian cancer.

Formulation

Some embodiments provided herein describe a pharmaceutical composition, wherein the composition further comprises one or more pharmaceutical carriers, excipients, auxiliaries, binders and/or diluents.

Any composition described herein optionally comprises minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In some embodiments, the composition further comprises one or more of lactose, dextrose, mannitol, pH buffering agents, antioxidant agents, preservative agents, tonicity adjusters or a combination thereof. Examples of pharmaceutically acceptable carriers that are optionally used include, but are not limited to aqueous vehicles, nonaqueous vehicles, antimicrobial agents, local anesthetics, suspending and dispersing agents, emulsifying agents, sequestering or chelating agents and other pharmaceutically acceptable substances.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein, in some embodiments, are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts are be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

In some embodiments, the pharmaceutical compositions described herein contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use are optionally prepared according to known method, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Suitable pharmaceutical carriers include inert diluents or fillers, water and various organic solvents. In some embodiments, the pharmaceutical composition contains additional ingredients such as flavorings, binders, excipients and the like. Thus for oral administration, tablets containing various excipients, such as citric acid are employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. In other embodiments, solid compositions of a similar type are employed in soft and hard filled gelatin capsules. Preferred materials, therefore, include lactose or milk sugar and high molecular weight polyethylene glycols. In certain embodiments where aqueous suspensions or elixirs are desired for oral administration, the active compound therein is combined with various sweetening or flavoring agents, coloring matters or dyes and, if desired, emulsifying agents or suspending agents, together with diluents such as water, ethanol, propylene glycol, glycerin, or combinations thereof.

In some embodiments, oily suspensions are formulated by suspending the active ingredient in a vegetable oil, for example arachis oil, olive oil, sesame oil or coconut oil, or in mineral oil such as liquid paraffin. In certain embodiments, the oily suspensions contain a thickening agent, for example beeswax, hard paraffin or cetyl alcohol. In further or additional embodiments, sweetening agents such as those set forth above, and flavoring agents are added to provide a palatable oral preparation. In other embodiments, these compositions are preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. In some embodiments, additional excipients, for example sweetening, flavoring and coloring agents, are also present. In further or additional embodiments, these compositions are preserved by the addition of an anti-oxidant such as ascorbic acid.

In some embodiments, pharmaceutical compositions are in the form of oil-in-water emulsions. In some embodiments, the oily phase is a vegetable oil, for example olive oil or arachis oil, or a mineral oil, for example liquid paraffin or mixtures of these. Suitable emulsifying agents include but are not limited to naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. In further or additional embodiments, the emulsions contain sweetening agents, flavoring agents, preservatives and antioxidants.

In some embodiments, pharmaceutical compositions described herein are in the form of a sterile injectable aqueous solution. Acceptable vehicles and solvents that are employed include but are not limited to water, Ringer's solution, phosphate buffered saline solution, U.S.P. and isotonic sodium chloride solution, ethanol, and 1,3-butanediol.

In addition, sterile, fixed oils are optionally employed as a solvent or suspending medium. For this purpose any bland fixed oil is optionally employed including synthetic mono- or diglycerides. Suitable lipophilic solvents or vehicles include fatty oils such as sesame oil, or synthetic fatty acid esters, such as ethyl oleate or triglycerides, or liposomes or other microparticulate systems may be used to target the agent to blood components or one or more organs. In some embodiments, the sterile injectable preparation is a sterile injectable oil-in-water microemulsion where the active ingredient is dissolved in the oily phase. In certain embodiments, the active ingredient is first dissolved in a mixture of soybean oil and lecithin. The oil solution then introduced into a water and glycerol mixture and processed to form a microemulsion. In further or additional embodiments, the injectable solutions or microemulsions are introduced into an individual's blood-stream by local bolus injection. Alternatively, in some embodiments, it is advantageous to administer the solution or microemulsion in such a way as to maintain a constant circulating concentration of the instant compound. In order to maintain such a constant concentration, a continuous intravenous delivery device are utilized. An example of such a device is the Deltec CADD-PLUS™ model 5400 intravenous pump.

In other embodiments, the pharmaceutical composition is in the form of a sterile injectable aqueous or oleagenous suspension for intramuscular and subcutaneous administration. In further or additional embodiments, this suspension is formulated using those suitable dispersing or wetting agents and suspending agents which have been mentioned above. In some embodiments, the sterile injectable preparation is a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose in some embodiments, any bland fixed oil is optionally employed including synthetic mono- or diglycerides. In addition, fatty acids such as oleic acid find use in the preparation of injectables.

In certain embodiments, pharmaceutical compositions are administered in the form of suppositories for rectal administration of the drug. These compositions are prepared by mixing the active ingredient with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

In some embodiments, the compounds or compositions described herein are delivered in a vesicle, such as a liposome. In further or alternative embodiments, the compounds and pharmaceutical compositions described herein are delivered in a controlled release system, or a controlled release system can be placed in proximity of the therapeutic target. In one embodiment, a pump is used.

For topical use, creams, ointments, jellies, solutions or suspensions, etc., containing a compound of Formula I, II, III, or IV is used. As used herein, topical application includes mouth washes and gargles.

In certain embodiments, pharmaceutical compositions are administered in intranasal form via topical use of suitable intranasal vehicles and delivery devices, or via transdermal routes, using transdermal skin patches. To be administered in the form of a transdermal delivery system, the dosage administration will be continuous rather than intermittent throughout the dosage regimen.

In some embodiments, the pharmaceutical composition described herein further comprises a cyclodextrin. In some embodiments, the cyclodextrin has a concentration (w/v) ranging from about 0.001% to about 50%. In other embodiments, the cyclodextrin has a concentration (w/v) ranging from about 2% to about 48%. In other embodiments, the cyclodextrin has a concentration (w/v) ranging from about 4% to about 45%. In other embodiments, the cyclodextrin has a concentration (w/v) ranging from about 10% to about 43%. In other embodiments, the cyclodextrin has a concentration (w/v) ranging from about 15% to about 40%. In other embodiments, the cyclodextrin has a concentration (w/v) ranging from about 20% to about 38%. In other embodiments, the cyclodextrin has a concentration (w/v) ranging from about 22% to about 37%. In other embodiments, the cyclodextrin has a concentration (w/v) ranging from about 25% to about 35%. In a preferred embodiment, the cyclodextrin has a concentration (w/v) ranging from about 28% to about 32%.

Some embodiments described herein provide a composition further comprising cyclodextrin, wherein the cyclodextrin has a concentration (w/v) of about 15%, 18%, 20%, 22%, 25%, 26%, 27%, 28%, 29%, 30%, 31%, 32%, 33%, 34%, 35%, 36%, 37%, or 38% when cyclodextrin derivative is SBE7-β-CD (Captisol®). In one embodiment, the cyclodextrin has a concentration (w/v) of about 30% when cyclodextrin derivative is SBE7-β-CD (Captisol®). In another embodiment, the solubility enhancer has a concentration (w/v) of about 29.4% when the cyclodextrin derivative is SBE7-β-CD (Captisol®).

Additional cyclodextrin derivatives suitable for use in intravenous compositions described herein are known in the art and are described in, e.g., U.S. Pat. Nos. 5,134,127 and 5,376,645 each of which is incorporated by reference herein for such disclosure. In addition, examples of suitable cyclodextrin derivatives are described below.

Suitable cyclodextrins and derivatives useful in certain embodiments of the compositions, methods and kits described herein include, for example, those described in Challa et al., AAPS PharmSciTech 6(2): E329-E357 (2005), U.S. Pat. Nos. 5,134,127, 5,376,645, 5,874,418, each of which is incorporated by reference herein for such disclosure. In some embodiments, suitable cyclodextrins or cyclodextrin derivatives for use in certain embodiments of the compositions, methods and kits described herein include, but are not limited to, α-cyclodextrins, β-cyclodextrins, γ-cyclodextrins, SAE-CD derivatives (e.g., SBE-α-CD, SBE-β-CD, SBE1-β-CD, SBE4-β-CD, SBE7-β-CD (Captisol®), and SBE-γ-CD) (Cydex, Inc. Lenexa, KS), hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethyl-hydroxypropyl ethers of α-, β- and γ-cyclodextrin; and the maltosyl, glucosyl and maltotriosyl derivatives of α-, β- and γ-cyclodextrin, which may contain one or more sugar residues, e. g. glucosyl or diglucosyl, maltosyl or dimaltosyl, as well as various mixtures thereof, e. g. a mixture of maltosyl and dimaltosyl derivatives. Specific cyclodextrin derivatives for use herein include hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, diethyl-β-cyclodextrin, glucosyl-α-cyclodextrin, glucosyl-β-cyclodextrin, diglucosyl-β-cyclodextrin, tri-O-methyl-β-cyclodextrin, tri-O-ethyl-β-cyclodextrin, tri-O-butyryl-β-cyclodextrin, tri-O-valeryl-β-cyclodextrin, and di-O-hexanoyl-β-cyclodextrin, as well as methyl-β-cyclodextrin, and mixtures thereof such as maltosyl-β-cyclodextrin/dimaltosyl-β-cyclodextrin. Any suitable procedure may be utilized for preparing such cyclodextrins including, e.g., those procedures described in U.S. Pat. No. 5,024,998, which is incorporated by reference herein for such disclosure. Other cyclodextrins suitable for use in certain embodiments of the compositions, methods and kits described herein include the carboxyalkyl thioether derivatives such as ORG 26054 and ORG 25969 by ORGANON (AKZO-NOBEL), hydroxybutenyl ether derivatives by EASTMAN, sulfoalkyl-hydroxyalkyl ether derivatives, sulfoalkyl-alkyl ether derivatives, and other derivatives, for example as described in U.S. Patent Application Nos. 2002/0128468, 2004/0106575, 2004/0109888, and 2004/0063663, or U.S. Pat. Nos. 6,610,671, 6,479,467, 6,660,804, or 6,509,323, each of which is specifically incorporated by reference herein for such disclosure.

Hydroxypropyl-β-cyclodextrin can be obtained from Research Diagnostics Inc. (Flanders, NJ). Exemplary hydroxypropyl-β-cyclodextrin products include Encapsin® (degree of substitution ~4) and Molecusol® (degree of substitution ~8); however, embodiments including other degrees of substitution are also available and are within the scope of the present invention.

Dimethyl cyclodextrins are available from FLUKA Chemie (Buchs, CH) or Wacker (Iowa). Other derivatized cyclodextrins suitable for use in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-β-cyclodextrins, e. g., succinyl-β- cyclodextrin (SCD). All of these materials can be made according to methods known in the art and/or are available commercially. Suitable derivatized cyclodextrins are disclosed in Modified Cyclodextrins: Scaffolds and Templates for Supramolecular Chemistry (Eds. Christopher J. Easton, Stephen F. Lincoln, Imperial College Press, London, UK, 1999) and New Trends in Cyclodextrins and Derivatives (Ed. Dominique Duchene, Editions de Sante, Paris, France, 1991).

Dosing

An isoflavonoid derivative described herein (e.g., a compound of Formula I, II, III, or IV) is optionally used in the preparation of medicaments for treating any of the diseases or conditions described herein in an individual in need of such treatment, and involves administration of pharmaceutical compositions containing at least one compound of Formula I, II, III, or IV or a pharmaceutically acceptable salt, in therapeutically effective amounts to said individual.

In the case wherein the patient's condition does not improve, upon the doctor's discretion the administration of the isoflavonoid derivative (e.g., a compound of Formula I, II, III, or IV) is optionally continued chronically and/or at a higher dose, to ameliorate or otherwise control or limit the cancer.

In the case wherein the patient's status does improve, upon the doctor's discretion the administration of the isoflavonoid derivative (e.g., a compound of Formula I, II, III, or IV) is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, when improvement of the patient's conditions has occurred, a maintenance dose is administered if necessary. Subsequently, the dosage or the frequency of administration, or both, is reduced, as a function of the cancer progression, to a level at which the improved condition is retained. In some embodiments, patients require intermittent treatment on a long-term basis upon any recurrence of symptoms and/or recurrence.

In some embodiments, the pharmaceutical compositions described herein are in unit dosage forms suitable for single administration of precise dosages. In unit dosage form, the formulation is divided into unit doses containing appropriate quantities of one or more compound of Formula I, II, III, or IV. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The daily dosages appropriate for the compounds are from about 0.1 mg to about 3000 mg, conveniently administered in divided doses, including, but not limited to, up to four times a day or in extended release form. Suitable unit dosage forms for oral administration include from about 0.1 to 1000 mg active ingredient, from about 0.1 to 500 mg active ingredient, from about 1 to 250 mg of active ingredient, from about 1 to about 100 mg active ingredient, from about 1 to about 75 mg active ingredient, from about 1 to about 50 mg active ingredient, from about 1 to about 30 mg active ingredient, from about 1 to about 20 mg active ingredient, or from about 1 to about 10 mg active ingredient. Such dosages are optionally altered depending on a number of variables, not limited to the activity of the compound used, the mode of administration, the requirements of an individual, the severity of the disease or condition being treated, and the judgment of the practitioner.

EXAMPLES

Example 1. Synthesis and Evaluation of Compound 31 (Scheme 3)

Compound 35. Hydrogenation of daidzein in ethanol and 1M potassium hydroxide solution with 10% Palladium on alumina catalyst and a hydrogen pressure of 0.5 bar in a stainless steel reactor. After the completion of the hydrogenation process the material was filtered and charged into a glass lined mild steel reactor where the pH was adjusted to 6.96 with 1M acetic acid. The resulting slurry was diluted further with water and then filtered to provide compound 35. The product was dried in vacuum oven at 60° C.

Compound 36. Compound 35 was protected as the bis-tert-butyldimethylsiloxy adduct by charging a glass lined mild steel reactor with compound 35, imidazole, N,N-dimethylformamide with agitation for 30 minutes. Tert-butyldimethylsilyl chloride was then added to the solution. At the completion of the process the material was transferred into a glass lined mild steel reactor containing water. The resulting slurry was filtered on a Nutche filter. The product was dried under vacuum at 50° C.

Compound 37. The Grignard reaction was completed by charging a stainless steel reactor with magnesium, THF, initiating a reaction with 1,2-dibromoethane, then adding 4-bromoanisole dissolved in THF. A solution of compound 36 in THF was then added over a period of 45 minutes maintaining a temperature <35° C. At the completion of the reaction excess magnesium was filtered off and the mixture was quenched with an ammonium chloride solution. After separating the phases, the organic layer was evaporated to a minimum volume, in vacuo. The resultant material was dissolved in ethanol and heated to reflux until conversion was complete. The mixture was then cooled to 0° C., and the product was collected by filtration. The product was dried under a stream of nitrogen.

Compound 38. The hydrogenation of the alkene moiety was effected by charging a stainless steel reactor with THF, 10% palladium on alumina catalyst and compound 37. The mixture was stirred under hydrogen at atmospheric pressure, until complete conversion was effected. The mixture was filtered and carried directly to the next step Compound 39. The deprotection was effected by transferring compound 38 in THF into a stainless steel reactor. Potassium fluoride was dissolved in water and added into the reactor. The mixture was heated at reflux until conversion was complete. The THF was distilled off, and the aqueous layer was extracted twice with ethyl acetate. The organic extracts were combined, and washed twice with calcium chloride (35% aq solution). The organic layer was washed four times with water, and the solvent was reduced in vacuo. Ethanol was added and the solution was cooled to effect crystallization. The resulting solid was collected via filtration. The product was dried under a stream of 85% humidity nitrogen.

Compound 32. Compound 39 was dissolved in refluxing chloroform, and added to a 1 M solution of boron tribromide in chloroform, in a glass-lined reactor. The reaction was stirred until complete, and then quenched with water. The pH of the mixture was adjusted to ≥12 with 3 N NaOH, and the organic layer was removed. Ethyl acetate was added to the aqueous solution, the pH was adjusted to 5.5-6.5 with 2N HCl, and the aqueous phase was removed. The organic solution was washed with water, then saturated brine, dried over sodium sulfate, and concentrated in vacuo. The residue was dissolved in isopropanol and concentrated in vacuo. The material was recrystallized from isopropanol and heptanes. The product was dried under vacuum at 50° C.

Compound 31. The chiral separation was performed via supercritical fluid chromatography (SFC), using a Thar SFC-350 System, and a Chiralpak AS-H column. Compound 32 was dissolved in a mixture of isopropanol and ethanol, applied to the column in portions via a stacked injection sequence, and eluted with a mixture of isopropanol, ethanol and supercritical $CO_2$. The eluent containing Compound 31 was collected and concentrated in vacuo. The residue was dissolved in ethanol and concentrated in vacuo, three times to replace residual isopropanol with ethanol. The product was milled and dried under vacuum with nitrogen purge at 60° C. The d-enantiomer of compound 31 was provided in >95% purity. The optical rotation of compound 31 was measured to be +24° at 27° C. (c=1 in ethanol)@99% enantiomeric excess.

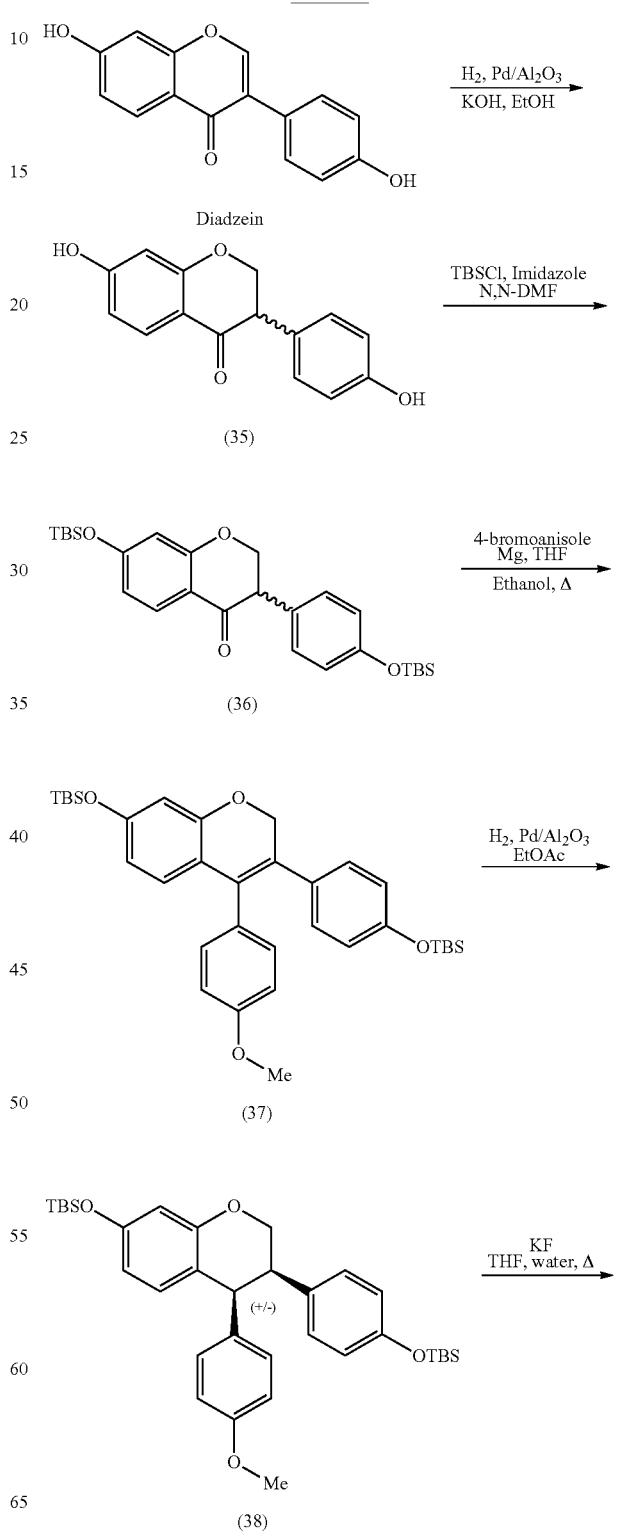

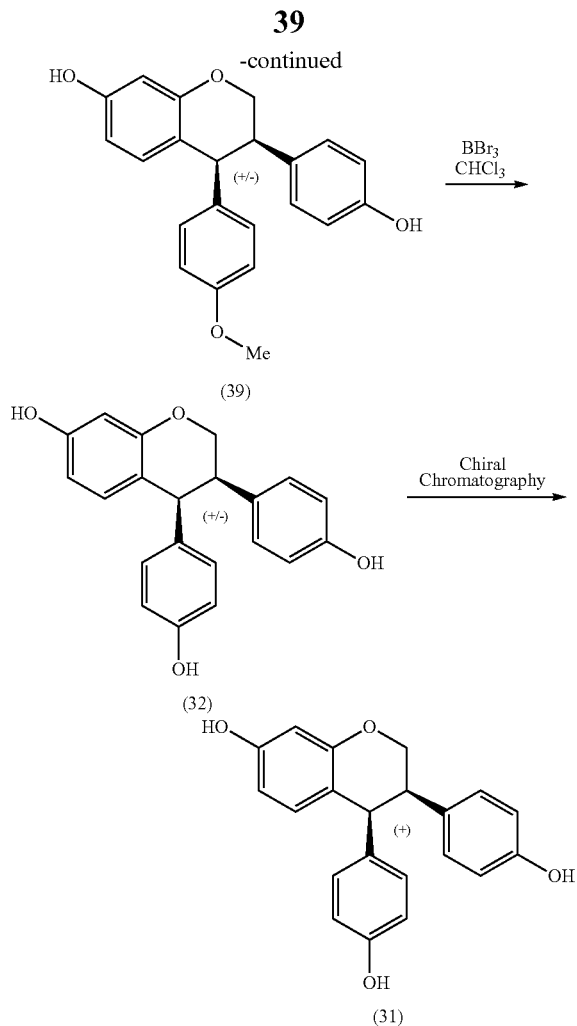

Example 2. Compounds

Any compound described herein may be synthesized according to the exemplary syntheses shown in Schemes 1, 2, or 3. $^1$H NMR data are provided for the following non-limiting compounds.

Compound 3. $^1$H NMR (400 MHz, $d_6$-DMSO) δ 9.32 (s, 1H); 9.19 (s, 1H); 6.82 (m, 1H); 6.65 (m, 1H); 6.56-6.50 (m, 4H); 6.41 (m, 1H); 6.36 (m, 1H); 6.31 (m, 1H); 6.28 (m, 1H); 4.23 (m, 1H); 4.17 (m, 1H); 4.12 (m, 1H); 3.43 (m, 1H); 2.01 (s, 3H).

Compound 4. $^1$H NMR (400 MHz, $d_6$-DMSO) δ 9.32 (s, 1H); 9.19 (s, 1H); 6.87 (m, 1H); 6.65 (m, 1H); 6.60-6.52 (m, 4H); 6.35 (m, 1H), 6.30 (m, 1H); 6.28 (m, 1H); 6.24 (m, 1H); 4.23 (m, 1H); 4.18 (m, 1H); 4.14 (m, 1H), 3.73 (s, 3H) 3.43 (m, 1H).

Compound 5. $^1$H NMR (400 MHz, $d_6$-Acetone) δ 8.24 (s, 1H); 8.16 (s, 1H); 8.10 (s, 1H); 6.62 (m, 2H); 6.58 (m, 2H); 6.54 (m, 3H); 6.44 (m, 2H); 6.39 (m, 1H); 4.38 (m, 1H); 4.20 (m, 1H); 4.14 (m, 1H); 3.42 (m, 1H); 2.13 (s, 3H).

Compound 6. $^1$H NMR (400 MHz, $d_6$-Acetone) δ 8.23 (s, 1H); 8.09 (s, 1H); 7.99 (s, 1H); 6.63 (m, 2H); 6.57 (m, 2H); 6.54 (m, 2H); 6.51 (m, 1H); 6.38 (m, 1H); 6.33 (m, 1H); 4.38 (m, 1H); 4.20 (m, 1H); 4.11 (m, 1H); 3.40 (m, 1H); 2.13 (s, 3H), 1.98 (s, 3H).

Compound 7. $^1$H NMR (400 MHz, $d_6$-Acetone) δ 8.10 (m, 2H); 6.63 (m, 2H); 6.61 (m, 1H); 6.57 (m, 2H); 6.54 (m, 1H); 6.41 (m, 1H), 6.38 (m, 1H); 6.36 (m, 1H); 4.38 (m, 1H); 4.21 (m, 1H); 4.14 (m, 1H); 3.73 (s, 3H); 3.42 (m, 1H); 2.14 (s, 3H), 1.95 (s, 3H).

Compound 8. $^1$H NMR (400 MHz, $d_4$-DMSO) δ 6.65 (m, 1H); 6.58 (m, 2H); 6.47 (m, 2H); 6.34 (m, 1H); 6.17 (s, 2H); 4.58 (s, 1H); 4.53 (s, 1H), 4.33 (m, 1H); 4.20 (m, 1H); 4.07 (m, 1H); 3.62 (s, 3H); 3.44 (m, 1H); 2.18 (s, 3H); 2.05 (s, 6H).

Compound 9. $^1$H NMR (400 MHz, $d_6$-CDCl$_3$) δ 6.69 (s, 1H); 6.23 (m, 3H); 6.51 (m, 2H); 6.39-6.34 (m, 3H); 4.62 (s, 1H); 4.59 (s, 1H), 4.34 (m, 1H); 4.25 (m, 1H); 4.16 (m, 1H); 3.49 (m, 1H); 2.19 (s, 3H); 2.06 (s, 3H).

Compound 10. $^1$H NMR (400 MHz, $d_6$-DMSO) δ 9.17 (s, 1H); 6.88 (m, 1H); 6.56-6.50 (m, 4H); 6.49 (m, 1H); 6.34 (m, 2H); 6.24 (m, 1H), 6.26 (m, 1H); 4.22 (m, 1H); 4.18 (m, 1H); 3.04 (s, 3H); 3.42 (m, 1H); 2.04 (s, 3H).

Compound 32. $^1$H NMR (400 MHz, $d_6$-Acetone) δ 8.33 (s, 1H); 8.26 (s, 1H); 8.19 (s, 1H); 6.71 (m, 1H); 6.63 (m, 2H); 6.58 (m, 2H); 6.55 (m, 2H); 6.45 (m, 2H), 6.39 (m, 1H); 6.35 (m, 1H); 4.34 (m, 1H); 4.14 (m, 1H); 4.12 (m, 1H); 3.42 (m, 1H).

Example 3: In Vitro Study of Anti-Proliferative Activity Against Cancer Cells

Tissue culture. The multidrug resistant primary epithelial ovarian cancer cell line R-182 TARA was a gift from Dr. Gil Mor (Yale University, New Haven, CT, USA). This cell line was derived by explant from ovarian tumors and cultured as previously described. All other cell lines were purchased from American Type Culture Collection (ATCC, Manassas, VA, USA) with the exception of MKN1, HuH-7, JHH-1, which were purchased from the Japanese Collection of Research Bioresources (JCRB, Osaka, Japan), and OE19 which was purchased from the European Collection of Cell Cultures (ECACC, Salisbury, UK).

The human non-small cell lung adenocarcinoma lines NCI-H1299 (CRL-5803), NCI-H460 (HTB-177), NCI-H358 (CRL-5807), NCI-H838 (CRL-5844), the human colorectal adenocarcinoma lines COLO 205 (CCL-222), HCT-15 (CCL-225) and the human gastric cancer cell line NCI-N87 (CRL-5822) were cultured in RPMI 1640 medium containing 2 g/L sodium bicarbonate (Hyclone/Invitrogen) supplemented with 2 mM L-glutamine (Gibco) 1 mM sodium pyruvate (Sigma), 10 mM HEPES (Sigma) and 4500 mg/L glucose (Sigma). The human non-small cell lung adenocarcinoma line NCI-H2126 (CCL-256) was cultured in DMEM:F12(1:1) (Hyclone/Invitrogen) containing 2.5 mM L-glutamine 2.4 g/L sodium bicarbonate supplemented with 5% fetal bovine serum (FBS), an additional 2 mM L-glutamine, 15 mM HEPES, 0.005 mg/ml insulin (Sigma), 0.01 mg/ml transferrin (Sigma), 30 nM sodium selenite (Sigma), 10 nM hydrocortisone (Sigma) and 10 nM beta-estradiol (Sigma). The human colorectal adenocarcinoma line HT-29 (HTB-38) and the human gastric cancer cell lines OE-19 (#96071721) and MKN1 (JCRB0252) were cultured in RPMI 1640 media supplemented with 2 mM L-glutamine.

The human colorectal adenocarcinoma line HCT-116 (CCL-247) and the human breast adenocarcinoma line SK-BR-3 (HTB-30) were cultured in McCoy's 5a Medium (Invitrogen) containing 1.5 mM L-glutamine and 2.2 g/L sodium bicarbonate. The human colorectal adenocarcinoma line SW620 (CCL-227) was cultured in Leibovitz's L-15 Medium (Invitrogen) containing 2.05 mM L-glutamine.

The human hepatocellular carcinoma lines HepG2 (HB-8065), SK-HEP-1 (HTB-52) and the normal human lung fibroblast line IMR-90 (CCL-186) were cultured in Minimum Essential Eagles Medium containing 2 mM L-glutamine, 2.2 g/L sodium bicarbonate, supplemented with 1 mM sodium pyruvate and 0.1 mM non-essential amino acids. The human hepatocellular carcinoma line JHH-1 (JCRB1062) was cultured in Williams E Medium (Invitrogen) containing 2.2 g/L sodium bicarbonate, supplemented with 2 mM L-glutamine. The hepatocellular carcinoma line HuH-7 (JCRB0403) was cultured in DMEM, supplemented with 2 mM L-glutamine.

The human gastric cancer cell line AGS (CRL-1739) was cultured in Hams F-12K (Kaighans modification) medium containing 2 mM L-glutamine, 2.5 g/L sodium bicarbonate and 2 mM sodium pyruvate. The human breast adenocarcinoma line MDA-MB-468 (HTB-132) was cultured in DMEM:F12 (1:1) medium containing 2.5 mM L-glutamine, 2.4 g/L sodium bicarbonate, supplemented with an additional 2 mM L-glutamine.

All cultures were supplemented with 10% FBS (unless stated otherwise), penicillin (100 U/ml) and streptomycin (100 μg/ml) and cultured at 37° C. in a humidified atmosphere of 5% CO2, with the exception of SW-620 which was cultured at 37° C. in standard humidified atmosphere.

Proliferation Assays. $IC_{50}$ values were determined for each cell line. Cells were seeded in 96-well plates at an appropriate cell density as determined from growth kinetics analysis and cultured for 5 days in the absence and presence of the test compounds. Cell proliferation was assessed after the addition of 20 μl of 3-4,5 dimethylthiazol-2,5-diphenyl tetrazolium bromide (MTT, 5 mg/ml in PBS, Sigma) for 5 hrs at 37° C. according to manufacturer's instructions. $IC_{50}$ values were calculated from semi-log plots of % of control proliferation on the y-axis against log dose on the x-axis.

Anti-proliferative Activity of Isoflavonoid Derivatives. $IC_{50}$ values were determined for each cell line after 120 h of exposure.

TABLE 1

| | | Compound | | | | | | | | |
|---|---|---|---|---|---|---|---|---|---|---|
| Indication | Cell Line | 31 | 5 | d-5 | l-5 | 7 | d-7 | l-7 | 6 | d-6 | l-6 |
| Prostate | PC3 | B | B | A | E | D | C | E | B | B | E |
| Prostate | DU145 | B | B | A | E | D | C | E | B | B | E |
| Prostate | LNCaP | B | B | A | E | D | D | E | C | B | E |
| CRC | COLO205 | D | D | C | E | E | E | E | D | D | E |
| Ovarian | A2780 | B | B | A | E | D | C | E | B | B | E |
| Ovarian | R-182 | A | B | A | E | D | C | E | B | A | E |
| Ovarian | CP70 | C | A | A | E | D | C | E | C | B | E |
| NSCLC | NCI-H460 | C | B | A | E | D | D | E | B | B | E |
| NSCLC | A549 | C | B | B | E | D | D | E | C | B | E |
| NSCLC | CALU3 | B | A | A | E | D | D | E | B | B | E |
| Liver | HepG2 | B | A | A | E | D | C | E | B | A | E |
| Liver | SK-Hep-1 | B | B | A | E | D | D | E | B | A | E |
| Liver | HuH-7 | B | B | A | E | D | C | E | B | B | E |
| Melanoma | A2058 | A | A | A | E | D | C | E | B | A | E |
| Melanoma | 4405 | B | B | A | E | D | D | E | B | B | E |
| Melanoma | MM200 | C | B | B | E | E | — | — | C | — | E |
| Breast | MDA-MB-468 | A | B | A | E | D | B | E | B | A | E |
| Breast | SKBR-3 | A | A | A | E | C | — | — | A | — | D |

Key: A: $IC_{50}$ ≤ 0.15 μM;
B: $IC_{50}$ = 0.15-0.50 μM;
C: $IC_{50}$ = 0.51-1.5 μM;
D: $IC_{50}$ = 1.6-10 μM;
E: $IC_{50}$ ≥ 10 μM

Example 4: In Vitro Study of Anti-Proliferative Activity of Compound 31

Compound 31, the d-isomer, exhibited superior anti-proliferative activity against various cancer cells over 120 hrs of exposure when compared with both the racemic (compound 32) and l-forms (compound 33). Activity data is provided is Table 2.

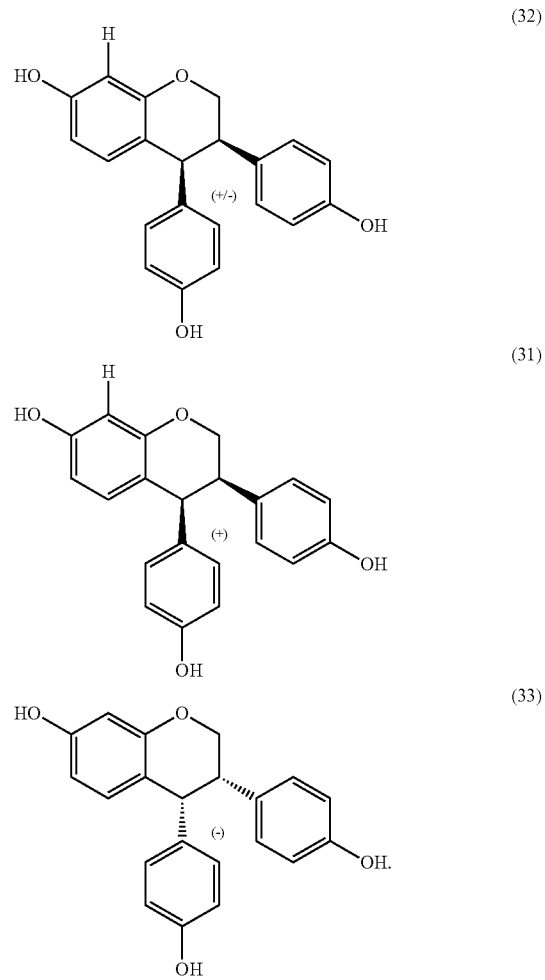

TABLE 2

| | | Compound | | |
|---|---|---|---|---|
| Indication | Cell Line | 32 | 31 | 33 |
| Prostate | PC3 | C | B | — |
| Ovarian | A2780 | C | B | E |
| Ovarian | CP70 | C | B | E |
| Melanoma | A2058 | B | A | — |
| Melanoma | MM200 | C | C | E |
| Breast | MDA-MB-468 | C | A | — |
| Breast | SKBR-3 | C | A | E |

Key: A: $IC_{50}$ ≤ 0.15 μM; B: $IC_{50}$ = 0.15-0.50 μM; C: $IC_{50}$ = 0.51-1.5 μM; D: $IC_{50}$ = 1.6-10 μM; E: $IC_{50}$ ≥ 10 μM

Example 5: In Vitro Assessment of Combination Compound 31 and Cancer Therapy

In vitro toxicity in normal and cancer cells. Cells were seeded in 96-well plates at an appropriate cell density as determined from growth kinetics analysis. Depending on the plating efficiency and lag phase of individual cell lines, cells were allowed to plate down prior to drug exposure. Intra-experimental single agent controls were included to ensure IC$_{50}$ values obtained for each cell line matched previous IC$_{50}$ determinations. Four analogue concentrations were employed in each analysis. Analogue concentrations used in each assay were chosen based on IC$_{50}$ values, which formed the top concentration of analogue used. Subsequent concentrations were chosen based on simple ½ or ⅒ dilutions of the top analogue concentration employed (i.e. 2, 1, 0.5, 0.25 µM). Nine ⅒ serial dilutions of chemotherapeutic were employed with the top chemotherapeutic concentration being 50 µM.

For combined analysis, analogue concentrations were held constant through ⅒ serial dilutions of chemotherapeutic in growth medium (top chemotherapeutic concentration employed was 50 µM). Combined cultures were cultured for 5 days.

The sequence of administration effect of each agent on chemotherapeutic IC$_{50}$ values was assessed by exposing plated cells to a single agent in sequence for 24 hr. To assess the isoflavonoid derivative→chemotherapeutic sequence, plated cells were first exposed to the appropriate analogue concentrations and incubated at 37° C. for 24 hr. Cells were washed with growth medium and then exposed to the appropriate chemotherapeutic concentrations and incubated for 24 hr. Cells were then washed and incubated for a further 3 days. To assess the chemotherapeutic→isoflavonoid derivative sequence, the procedure was reversed.

Cell proliferation was assessed after the addition of 20 µl of 3-4,5 dimethylthiazol-2,5-diphenyl tetrazolium bromide (MTT, 2.5 mg/ml in PBS, Sigma) for 3-4 hrs at 37° C. according to manufacturer's instructions. IC$_{50}$ values were calculated from semi-log plots of % of control proliferation on the y-axis against log dose on the x-axis.

3-D model analysis of the cytotoxic interaction between drug A and drug B enables the representation of predicted inhibitory effect of two drugs in combination in 3 dimensions to reveal actual regions of synergy or antagonism. The 3D synergy plots are based on a theory of "Theoretical Additivity" (TA or observed synergy) as outlined by Kanzawa et al. Theoretical Additivity was calculated from the cytotoxicities of drug A and drug B as monotherapies using the following formula which assumes the drugs are mutually exclusive inhibitors:

$$TA_{(1)} = \frac{(f_a)_A - (f_a)_B - 2(f_a)_A(f_a)_B}{1 - (f_a)_A(f_a)_B}$$

Where $(f_a)A$=fraction of cells affected by drug A
$(f_b)B$=fraction of cells affected by drug B The TA is calculated for each combination of drug concentrations and subtracted from the observed experimental effect for each combination to give a measurement of synergistic or enhanced action. A positive difference indicates that more cells are affected by the drug combination than would be expected in theory if the two drugs were administered together—hence synergism. A negative difference indicates that less cells were affected than theoretically expected—hence antagonism.

Combination index (CI) analysis, which employs the median-effect principle correlating drug dose to cytotoxicity, was also employed to assess synergy. The median-effect equation is utilized to calculate the dose of a drug that inhibits "x" percent of cells (Chou and Talalay, 1984).

$$D = Dm[f_a/(1-f_a)]^{1/m}$$

Where D is dose of drug, Dm is median effect signifying potency, fa is fraction affected by dose and m is the sigmoidicity of the dose effect curve.

For two drugs with mutually nonexclusive mechanisms of action (D)1 and (D)2, CI is then calculated as:

$$CI = \frac{(D)_1}{(D_x)_1} + \frac{(D)_2}{(D_x)_2} + \frac{(D)_1(D)_2}{(D_x)_1(D_x)_2}$$

In vitro Assessment of Combination of Optically Active Compound 31 and Carboplatin. Combination studies employed both 24 hr concurrent exposure, and 24 hr sequential exposure (racemic compound 32→Carboplatin) regimens. In both studies, four analogue concentrations (0.25, 0.5, 1 and 5 µM) were held constant against titrated carboplatin. When 1 and 5 µM of compound 32 was assessed in combination with the lowest concentration of carboplatin employed in this study (0.4 µM), no IC$_{50}$ for carboplatin was achieved due to the high levels of cell kill observed (30-40% of control). The data indicates that inclusion of 0.5 µM of compound 32 enhanced the anti-cancer effect of carboplatin by 7-11 fold depending on exposure regimen, and ~1.5-2 fold when 0.25 µM of compound 32 was employed.

When the compound 31-carboplatin combination was assessed at 0.5, 1 and 5 µM of compound 31 plus the lowest concentration of carboplatin employed in this study (0.4 µM), no IC$_{50}$ for carboplatin was achieved due to high cell kill levels observed at 25-40% of control. The data indicates that, depending on exposure regimen, inclusion of 0.25 µM of compound 31 enhanced the anti-cancer effect of carboplatin by 7-11 fold.

Using the 3D method of Kanzawa, it was found that the combination of 0.5 µM of compound 32 and 12.5 µM carboplatin yielded maximal level of inhibition of cell proliferation compared with respective controls. This effect was observed at concentrations ranging from 1.5-100 µM carboplatin (depending of the exposure regimen) and at all concentration of compound 32. In comparison, maximal activity enhancement between compound 31 and carboplatin was also observed 12.5 µM carboplatin but at a 2-fold lower dilution of compound 31 (0.25 µM). While the concentration range where activity enhancement was observed is not as wide as that observed with compound 32 (particularly at higher compound 31 concentrations), this is due to the higher potency of compound 31 at 1 and 5 µM. The data indicates that compound 31 is superior in its ability to augment carboplatin toxicity against A2780 ovarian cancer cells compared with compound 32. It is important to note that compound 33 did not impart any activity enhancement or antagonistic effect when assessed in combination with carboplatin against the A2780 cell line.

Example 6: Relative Potencies of the Compound 31 and Compound 34 to Augment Carboplatin Toxicity in Ovarian Cancer Cells (A2780)

Sequential exposure (24 h) of A2780 cells to 0.25 µM of compound 31 followed by carboplatin resulted in superior retardation of A2780 cell proliferation when compared with the compound 34 (0.25 µM). Similarly, exposure of A2780 cells to 0.5 µM of compound 31 in combination with carboplatin further enhanced the potency of the inhibition of proliferation and this potency was superior to that observed with 0.5 µM of compound 34. These data demonstrate that the compound 31-carboplatin combination is more efficacious at inhibiting A2780 cancer cell proliferation when compared with the compound 34-carboplatin combinations.

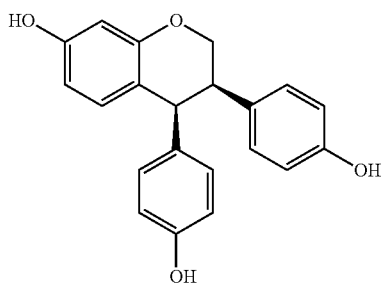

(34)

Example 7. Intravenous Composition of Compound 31

Compound 31 is dissolved in an 8% solution of Captisol® in water, at a rate of 10 mg/mL, well below its solubility limit of 27.9 mg/mL at 25° C. (20% Captisol®). Formulation is carried out under aseptic conditions. Sterility is achieved by terminal filtration through a 0.22 micron filter.

Example 8: Intravenous Composition of Compound 5

An exemplary formulation according to the invention is made according to the following general procedure. SBE7-β-CD is dissolved in water to form a solution containing about 30% w/v of cyclodextrin. Compound 5 is added to the SBE7-β-CD containing solution until a concentration of about 35 mg/mL compound 5 is reached. A formulation evaluated in animal and human clinical studies and comprising the following components in the amounts indicated is prepared as indicated above. The pH of the solution is not adjusted and no antioxidants or preservatives are included.

Example 9: Intravenous Composition of Compound 6

SBE7-β-CD is dissolved in water to form a solution containing about 30% w/v of SBE7-β-CD. Disodium ethylenediaminetetraacetate is added to the SBE7-β-CD solution at 0.01% w/v and dissolved. Compound 6 is added to the SBE7-β-CD containing solution with stirring until a concentration of about 35 mg/mL compound 6 is reached. The pH is adjusted to 7-8.5 with sodium hydroxide. The solution is purged with nitrogen gas then filtered through a 0.22 micron pore size filter prior to administration.

Example 10: Treatment for Breast Cancer

Human Clinical Trial of the Safety and/or Efficacy of Isoflavonoid for Breast Cancer Therapy Objective: To compare the safety and pharmacokinetics of administered composition comprising compound 5, 6, 7, d-5, d-6, d-7, or 31.

Study Design: This study will be a Phase I, single-center, open-label, randomized dose escalation study followed by a Phase II study in breast cancer patients. Patients should not have had exposure to the compound prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 5, 6, 7, d-5, d-6, d-7, or 31 on days 1, 8, and 15 of each 28-day cycle. Doses of compound 5, 6, 7, d-5, d-6, d-7, or 31 may be held or modified for toxicity based on assessments as outlined below. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 5, 6, 7, d-5, d-6, d-7, or 31 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of the compound. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep-.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 11: Treatment for Ovarian Cancer

Human Clinical Trial of the Safety and/or Efficacy of Isoflavonoid for Ovarian Cancer Therapy Objective: To compare the safety and pharmacokinetics of administered composition comprising compound 5, 6, 7, d-5, d-6, d-7, or 31.

Study Design. This study will be a Phase I, single-center, open-label, randomized dose escalation study followed by a Phase II study in ovarian cancer patients. Patients should not have had exposure to the compound prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. compound 5, 6, 7, d-5, d-6, d-7, or 31 on days 1, 8, and 15 of each 28-day cycle. Doses of the compound may be held or modified for toxicity based on assessments as outlined below. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 5, 6, 7, d-5, d-6, d-7, or 31 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of the compound. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep-.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

What is claimed is:

1. A pharmaceutical composition comprising d-cis-3-(4-hydroxyphenyl)-4-(4-hydroxyphenyl)-8-methylchroman-7-ol in at least 95% enantiomeric excess, and one or more pharmaceutically acceptable carriers, excipients, auxiliaries, binders and/or diluents.

2. The pharmaceutical composition of claim 1, wherein the d-cis-3-(4-hydroxyphenyl)-4-(4-hydroxyphenyl)-8-methylchroman-7-ol is provided in at least 99% enantiomeric excess.

3. The pharmaceutical composition of claim 1, wherein the d-cis-3-(4-hydroxypheny 1)-4-(4-hydroxyphenyl)-8-methylchroman-7-ol is provided in 95% to 99.9% enantiomeric excess.

4. The pharmaceutical composition of claim 1, comprising d-cis-3-(4-hydroxyphenyl)-4-(4-hydroxyphenyl)-8-methylchroman-7-ol in at least 95% enantiomeric excess, and a pharmaceutically acceptable carrier.

5. The pharmaceutical composition of claim 4, wherein the pharmaceutically acceptable carrier is an aqueous vehicle.

6. The pharmaceutical composition of claim 5, wherein the aqueous vehicle comprises water, Ringer's solution, phosphate buffered saline solution, isotonic sodium chloride solution, ethanol, or 1,3-butanediol.

7. The pharmaceutical composition of claim 5, wherein the aqueous vehicle is sterile water.

8. The pharmaceutical composition of claim 1, wherein the pharmaceutical composition comprises a pharmaceutically acceptable carrier comprising an aqueous vehicle and an auxiliary comprising a solubility enhancing agent.

9. A method of treating cancer in an individual in need of cancer therapy, the method comprising administering to the individual a composition comprising d-cis-3-(4-hydroxyphenyl)-4-(4-hydroxyphenyl)-8-methylchroman-7-ol provided in at least 95% enantiomeric excess.

10. The method of claim 9, wherein the d-cis-3-(4-hydroxyphenyl)-4-(4-hydroxyphenyl)-8-methylchroman-7-ol is provided in at least 99% enantiomeric excess.

11. The method of claim 9, wherein the d-cis-3-(4-hydroxyphenyl)-4-(4-hydroxyphenyl)-8-methylchroman-7-ol is provided in 95% to 99.9% enantiomeric excess.

12. The method of claim 9, wherein the cancer has lost sensitivity to a chemotherapeutic agent, anti-cancer agent, or radiation therapy.

13. The method of claim 9, wherein the cancer is bladder cancer, breast cancer, colon cancer, rectal cancer, endometrial cancer, kidney cancer, leukemia, lung cancer, melanoma, non-Hodgkin lymphoma, ovarian cancer, pancreatic cancer, prostate cancer, thyroid cancer, or brain cancer.

14. The method of claim 9, wherein the cancer is breast cancer, colon cancer, rectal cancer, or lung cancer.

15. The method of claim 9, wherein the cancer is metastatic colorectal cancer or metastatic HER2-negative breast cancer.

16. A kit comprising a composition comprising d-cis-3-(4-hydroxyphenyl)-4-(4-hydroxypheny 1)-8-methy lchroman-7-ol provided in at least 95% enantiomeric excess; and a sealable, plastic infusion bag.

17. The kit of claim 16, wherein the d-cis-3-(4-hydroxyphenyl)-4-(4-hydroxyphenyl)-8-methylchroman-7-ol is provided in at least 99% enantiomeric excess.

18. The kit of claim 16, wherein the d-cis-3-(4-hydroxyphenyl)-4-(4-hydroxyphenyl)-8-methylchroman-7-ol is provided in 95% to 99.9% enantiomeric excess.

* * * * *

UNITED STATES PATENT AND TRADEMARK OFFICE
CERTIFICATE OF CORRECTION

PATENT NO. : 12,329,739 B2
APPLICATION NO. : 18/363328
DATED : June 17, 2025
INVENTOR(S) : George Jeoffreys et al.

Page 1 of 1

It is certified that error appears in the above-identified patent and that said Letters Patent is hereby corrected as shown below:

In the Claims

In Claim 3, Column 48, Lines 48-49, replace:
"d-cis-3-(4-hydroxypheny l)-4-(4-hydroxyphenyl)-8-methylchroman-7-ol"
With:
--d-cis-3-(4-hydroxyphenyl)-4-(4-hydroxyphenyl)-8-methylchroman-7-ol--;

In Claim 16, Column 50, Lines 8-10, replace:
"d-cis-3-(4-hydroxyphenyl)-4-(4-hydroxypheny 1)-8-methy lchroman-7-ol"
With:
--d-cis-3-(4-hydroxyphenyl)-4-(4-hydroxyphenyl)-8-methylchroman-7-ol--.

Signed and Sealed this
Nineteenth Day of August, 2025

Coke Morgan Stewart
*Acting Director of the United States Patent and Trademark Office*